United States Patent [19]
Zagursky et al.

[11] Patent Number: 5,955,596
[45] Date of Patent: Sep. 21, 1999

[54] **NUCA PROTEIN OF *HAEMOPHILUS INFLUENZAE* AND THE GENE ENCODING THAT PROTEIN**

[75] Inventors: Robert J. Zagursky, Victor; Peggy Ooi, Mendon, both of N.Y.

[73] Assignee: American Cyanamid Company, Madison, N.J.

[21] Appl. No.: 08/687,865

[22] Filed: Jul. 26, 1996

[51] Int. Cl.⁶ ..................................................... C07H 21/04
[52] U.S. Cl. ..................... 536/23.7; 536/23.1; 435/172.1; 435/320.1; 424/190.1; 424/200.1; 424/256.1; 530/350
[58] Field of Search .................................. 536/23.7, 23.1; 435/320.1, 172.1; 424/256.1, 190.1, 200.1; 530/350

[56] References Cited

PUBLICATIONS

Nowak, R., Science, 269, 468–70 (Jul. 28, 1995).
Fleischmann, R.D., et al., Science, 269, 496–512 (Jul. 28, 1995).
Smith, H.O., et al., Science, 269, 538–540 (Jul. 28, 1995).

*Primary Examiner*—James C. Housel
*Assistant Examiner*—Jennifer Shaver
*Attorney, Agent, or Firm*—Alan M. Gordon

[57] ABSTRACT

A protein from *H. influenzae* designated NucA is isolated and purified. The NucA protein has the amino acid sequence of amino acids 26–603 of SEQ ID NO:2 or a biologically equivalent amino acid sequence thereof. Amino acids 1–25 of SEQ ID NO:2 are the signal peptide, which is cleaved during processing of the mature protein. The NucA protein has a molecular weight of approximately 63,000 Daltons as measured on a 12% SDS-PAGE gel and possesses 5'-nucleotidase activity. The NucA protein is obtained by isolation and purification from the *H. influenzae* organism, by chemical synthesis or by recombinant expression by an isolated and purified nucA DNA sequence which encodes the NucA protein. Such a DNA sequence hybridizes under standard high stringency Southern hybridization conditions with a DNA sequence encoding the NucA protein of *H. influenzae* having the amino acid sequence of amino acids 26–603 of SEQ ID NO:2 or a biologically equivalent amino acid sequence thereof. The NucA protein is used to prepare a vaccine composition which elicits a protective immune response in a mammalian host to protect the host against disease caused by *H. influenzae*.

13 Claims, 15 Drawing Sheets

NUCA PROTEIN OF *HAEMOPHILUS INFLUENZAE* AND THE GENE ENCODING THAT PROTEIN

FIELD OF THE INVENTION

This invention relates to a 63,000 Dalton protein produced by *Haemophilus influenzae* designated NucA, and to the nucA gene which encodes that protein.

BACKGROUND OF THE INVENTION

Nontypable *Haemophilus influenzae* (NTHi) is a strictly human commensal organism found in the upper respiratory tracts of up to 80% of healthy adults (Bibliography entry 1). It is a leading cause of otitis media and respiratory infections in children, including pneumonia and sinusitis (2). Since NTHi strains are unencapsulated, the existing vaccines for *H. influenzae*, which are based on the capsular structure of Type b (Hib), are ineffective. Hence a vaccine specific for NTHi organisms is needed and potential vaccine components have focused on surface exposed antigens like outer-membrane proteins.

SUMMARY OF THE INVENTION

Accordingly, it is an object of this invention to isolate and purify an additional protein from *H. influenzae* and to test whether the protein is a viable vaccine candidate in appropriate model systems.

It is a further object of this invention to isolate and clone the gene encoding such a protein and to express the protein recombinantly.

These and other objects of the invention as discussed below are achieved by the isolation and purification of a protein from *H. influenzae* which is designated NucA, as well as peptides of NucA protein comprising an epitope or epitopes thereof. The isolated and purified NucA protein of *H. influenzae* has the amino acid sequence of amino acids 26–603 of SEQ ID NO:2 or a biologically equivalent amino acid sequence thereof. Amino acids 1–25 of SEQ ID NO:2 are the signal peptide, which is cleaved during processing of the mature protein. The NucA protein has a molecular weight of approximately 63,000 Daltons as measured on a 12% SDS-PAGE gel and possesses 5'-nucleotidase activity.

In one embodiment of the invention, the NucA protein is obtained by isolation and purification from the *H. influenzae* organism. In a preferred embodiment of the invention, the NucA protein is recombinantly expressed by an isolated and purified nucA DNA sequence which encodes that protein.

The invention includes an isolated and purified DNA sequence comprising a DNA sequence which hybridizes under standard high stringency Southern hybridization conditions with a DNA sequence encoding the NucA protein of *H. influenzae* having the amino acid sequence of amino acids 26–603 of SEQ ID NO:2 or a biologically equivalent amino acid sequence thereof.

Examples of such biologically equivalent NucA sequences are those wherein the amino acid sequence of amino acids 26–603 of SEQ ID NO:2 is modified by one or more of the following amino acid residue changes selected from the group consisting of K79E, N186K, S262G, V294A, E305Q, K327R, T337A, D360Y, R376H or V436I.

The invention further includes such a DNA sequence which hybridizes under standard high stringency Southern hybridization conditions with a DNA sequence having the nucleotide sequence of nucleotides 304–2037 of SEQ ID NO:1.

In order to obtain expression of the NucA protein, the DNA sequence is first inserted into a suitable plasmid vector. A suitable host cell is then transformed or transfected with the plasmid. In an embodiment of this invention, the host cell is Escherichia coli strain InvαF'. The host cell is then cultured under conditions which permit the expression of said NucA protein by the host cell.

In another embodiment of this invention, the isolated and purified NucA protein or a peptide of NucA protein comprising an epitope or epitopes thereof, is used to prepare a vaccine composition which elicits a protective immune response in a mammalian host. The vaccine composition may further comprise an adjuvant, diluent or carrier. Examples of such adjuvants include aluminum hydroxide, aluminum phosphate, MPL™, Stimulon™ QS-21, and IL-12. The vaccine composition is administered to a mammalian host in an immunogenic amount sufficient to protect the host against disease caused by *H. influenzae*.

BRIEF DESCRIPTION OF THE FIGURES

FIG. 4 (bottom) depicts a limited genomic restriction map of the nucA gene.

Top—The approximately 3 kb Nsi1 circle contained sequence information upstream of the P1 nucA region. PCR amplification using primer pairs 4313ext & 4102ext produced an approximately 2 kb DNA fragment.

Middle—The approximately 4.3 kb EcoRI circle would contain sequence information upstream of the P1 nucA region. PCR amplification using primer pairs 4121fwd & 4122ext should produce an approximately 4 kb DNA fragment. No DNA fragment of this size was observed.

Bottom—The approximately 1.6 kb EcoRI circle would contain sequence information downstream of the nucA coding region. PCR amplification using primer pairs 4102ext &

4313ext should produce an approximately 0.7 kb DNA fragment. In fact, an approximately 1.3 kb fragment was obtained.

Figure 6:
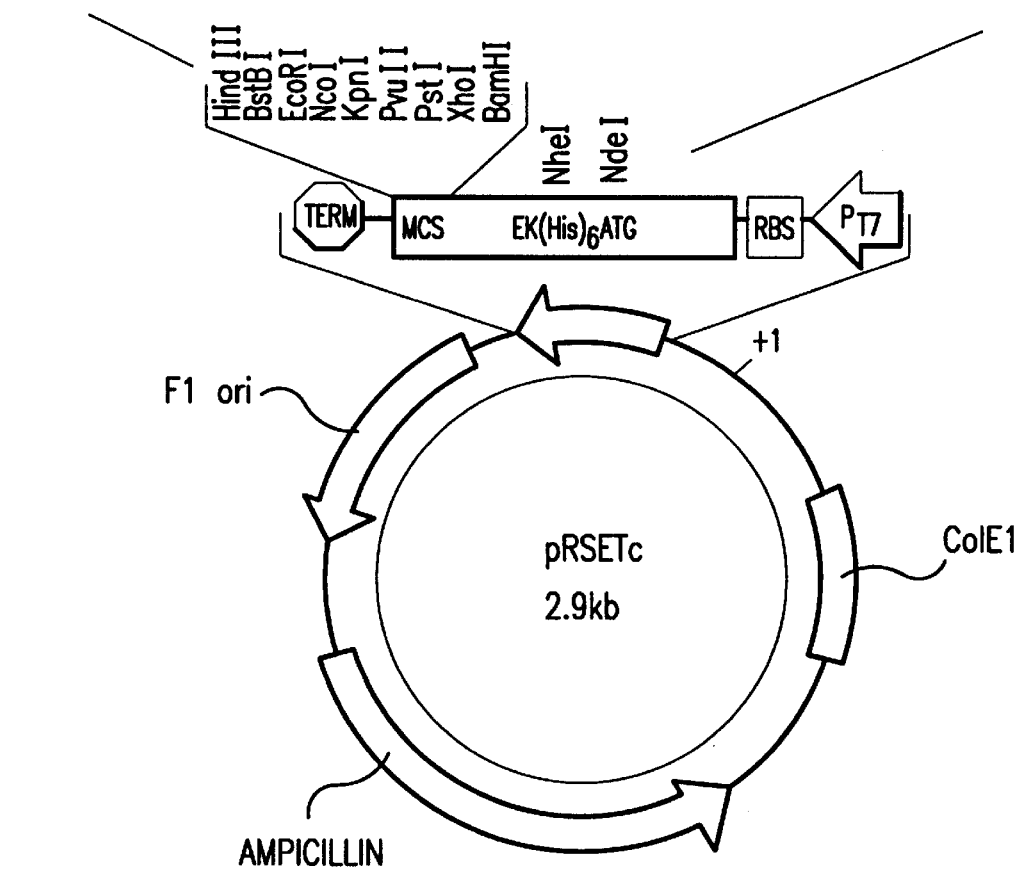

FIG. 6 depicts the pRSETC expression vector, including the DNA sequence surrounding the cloning sites downstream of the gene 10 T7 promoter ($P_{T7}$). The restriction enzyme DNA recognition sites, Nde1, Nhe1, BamH1, and HindIII, are underlined. The protein start and reading frame is shown below the DNA sequence, as well as the enterokinase cleavage site (EK Cleavage).

Figure 7:
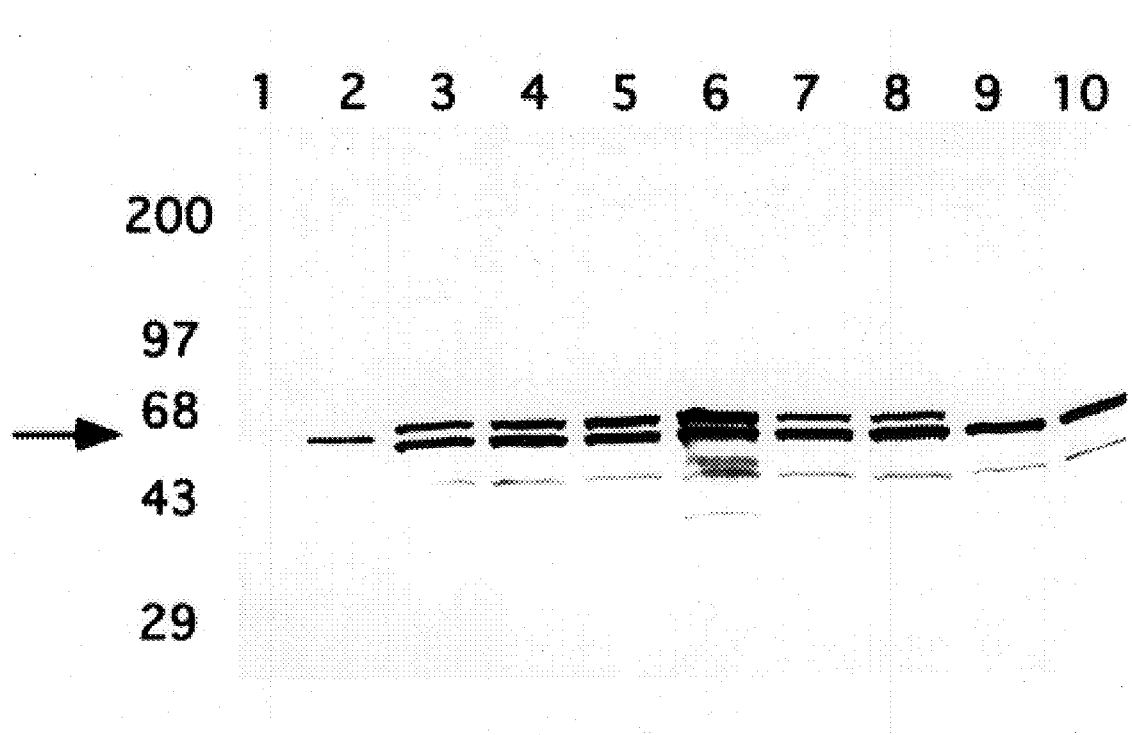

FIG. 7 depicts a Western blot on cell lysates from the expression products of pPX644 probed with rabbit polyclonal antibodies. Lane 1: Prestained high molecular weight protein standards (200, 97.4, 68, 43, 29, 18.4 and 14.3 kD)(Gibco BRL); Lane 2: NucA purified native protein standard; Lanes 3&4: BL21(DE3)pLysS/pPX644, isolate #1, uninduced and induced, respectively; Lanes 5&6: BL21 (DE3)pLysS/pPX644, isolate #5, uninduced and induced, respectively; Lanes 7&8: BL21(DE3)pLysS/pPX644, isolate #7, uninduced and induced, respectively; Lanes 9&10: BL21(DE3)pLysS/pRSETC, uninduced and induced, respectively. The arrow shows the migration of NucA.

Figure 8A:
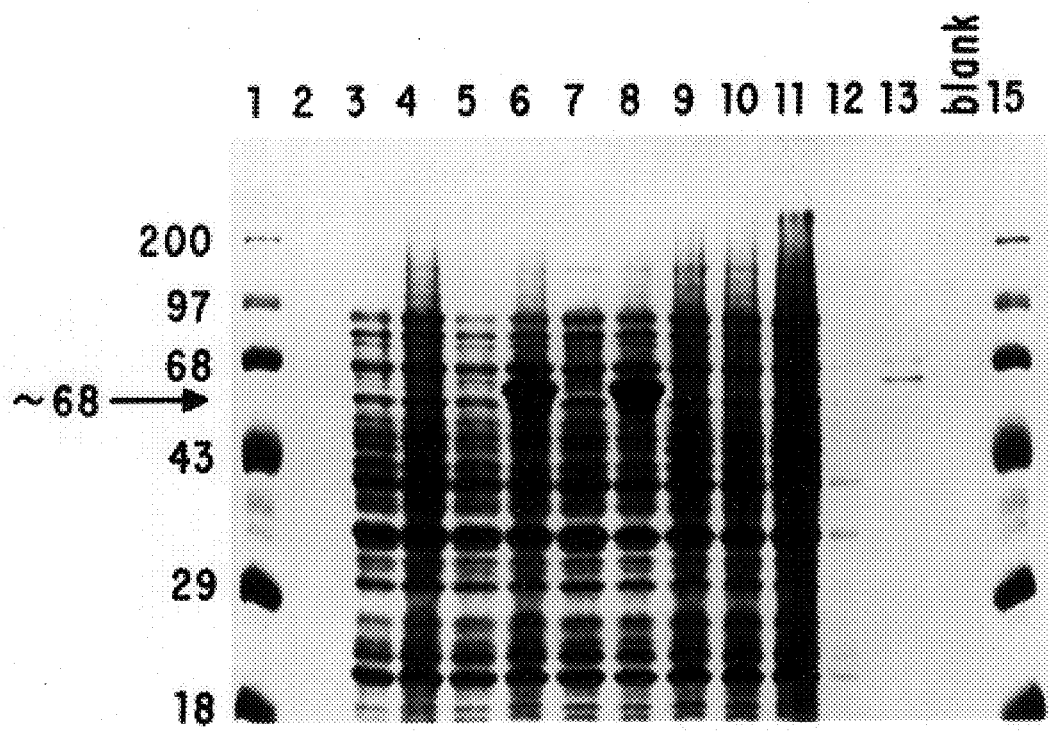
Figure 8B:

FIG. 8A depicts a Coomassie stained 12% gel and FIG. 8B depicts a Western blot on cell lysates from nucA mature sequence fusion clones #1–3 of pPX693 showing uninduced and induced lysates, probed with rabbit polyclonal antibodies. A second clone of pPX707(ompT signal sequence) is also depicted. Lane 1—BRL high molecular weight protein standards with apparent molecular weights as shown in the Figure; Lane 2—nNucA; Lane 3—pPX707, clone #2, uninduced; Lane 4—pPX707, clone #2, induced; Lane 5—pPX693, clone #1, uninduced; Lane 6—pPX693, clone #1, induced; Lane 7—pPX693, clone #2, uninduced; Lane 8—pPX693, clone #2, induced; Lane 9—pPX693, clone #3 (nucA in wrong orientation); Lane 10—pPX693, clone #3, induced, showing no induction of the approximately 68 kD band; Lane 11—pPX693, clone #3, induced, but at $O.D._{600}$ of 1.7 instead of 1.0; Lane 12—lysate from an induced vector alone (PRSETC) culture, negative control; Lane 13—a purified preparation of rNucA from pPX644; Lane 14—blank; Lane 15—BRL low molecular weight standards.

Figure 9:
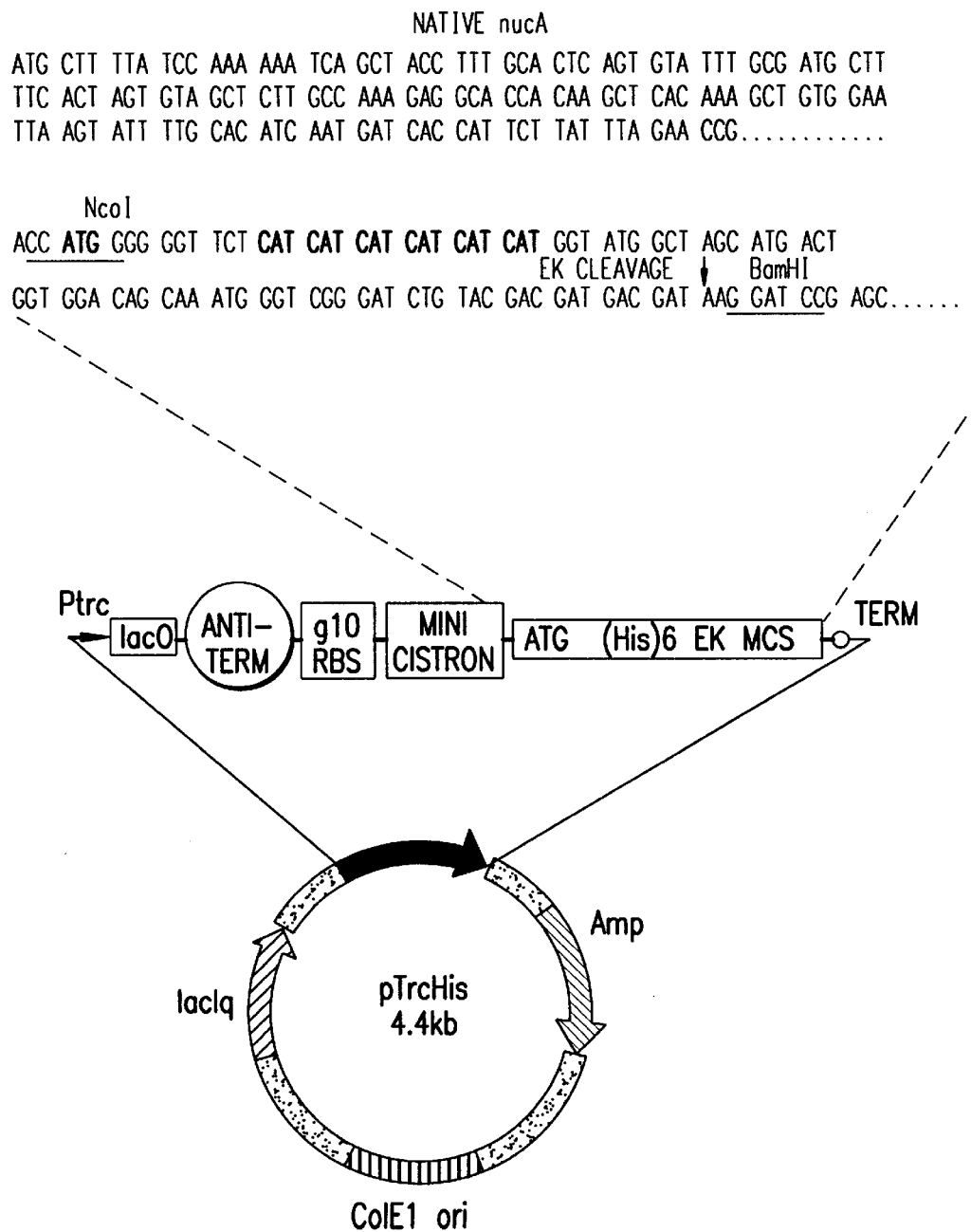

FIG. 9 depicts the features of the pTrcHisC vector, together with the nucA signal and partial mature sequences to show the sites of insertion into the vector in the construction of pPX691. The first three lines of sequence in FIG. 9 represent a partial native nucA sequence starting at the first ATG of the signal sequence (SEQ ID NO:22) and continuing into the mature sequence for 78 bases. The next two lines of sequence represent the coding sequence of the vector (SEQ ID NO:23) encompassing the NcoI restriction site (which contains the ATG start site), polyHis region, enterokinase cleavage site and the BamHI site of the multiple cloning region, in the vector. The plasmid contains lacI$^q$ in order to repress the strong inducible trc promoter, such that expression is turned off (there is a low basal level from leak through) until induction.

Figure 10A:
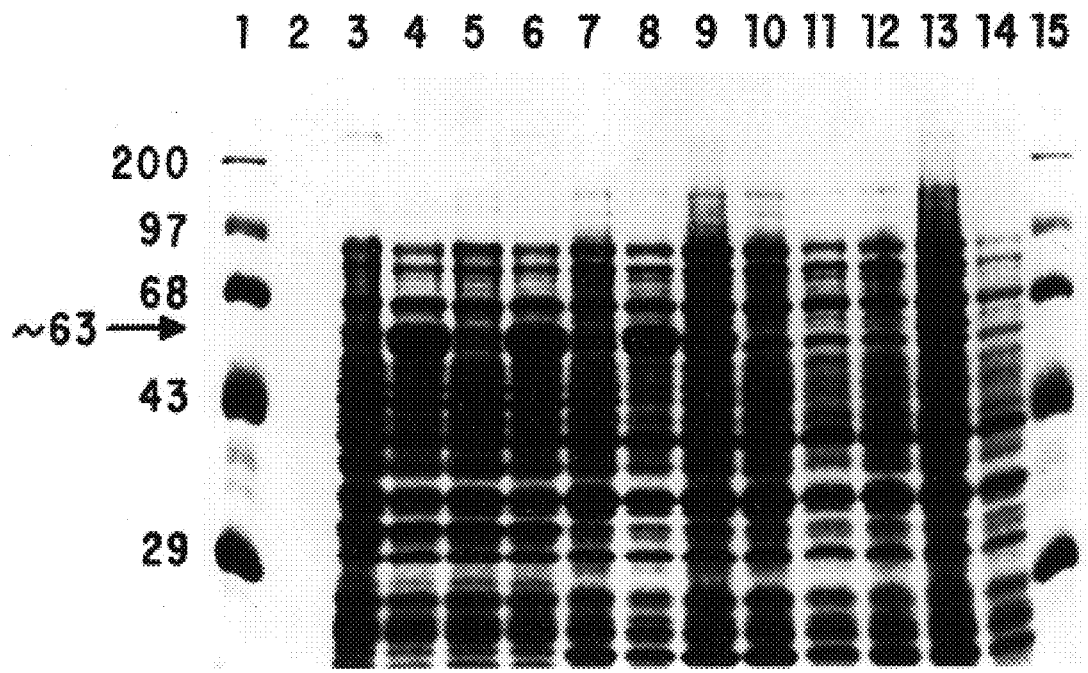
Figure 10B:
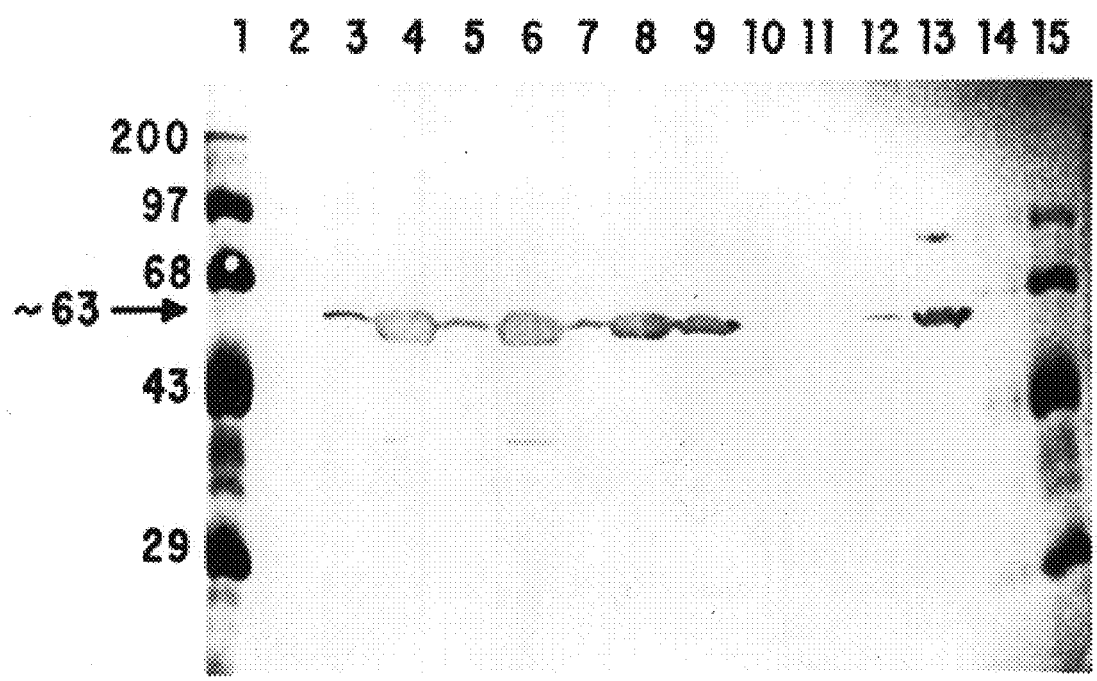

FIG. 10A depicts a Coomassie stained gel and FIG. 10B depicts a Western blot on cell lysates from pPX691, pPX692 and pPX707 which are constructs with either the native (pPX691 and 692) or ompT (pPX707) signal sequence in different vectors and host strains. Included are negative controls of pRSETC which is the vector for pPX692. The additional induced lane (#9 from left) under pPX692 is from a culture induced at $O.D._{600}$=1.5 instead of 1.0, showing a decrease in NucA protein expression. The uninduced and induced pRSETC lysates in lanes 10 and 11 are from a clone with no inserted nucA, while the induced pRSETC lysate in lane 14 is from vector transformed into a similar host strain. Lanes 1 and 15—apparent molecular weight standards are as listed on the Figure (200, 97, 68, 43 and 29 kD; Lane 2—native NucA protein (but not enough protein was present to be visualized with Coomassie staining); Lanes 3 and 5 uninduced cell lysates from clones #14 and #15 of pPX691, respectively; Lanes 4 and 6—induced cell lysates of the same pPX691 clones; Lane 7—uninduced cell lysate from clone #11 of pPX692; Lanes 8 and 9 cell lysates of the same culture but induced at $O.D._{600}$ of 0.9 and 1.5, respectively; Lane 12—pPX707, clone #1, uninduced; Lane 13—pPX707, clone #1, induced.

Figure 11:
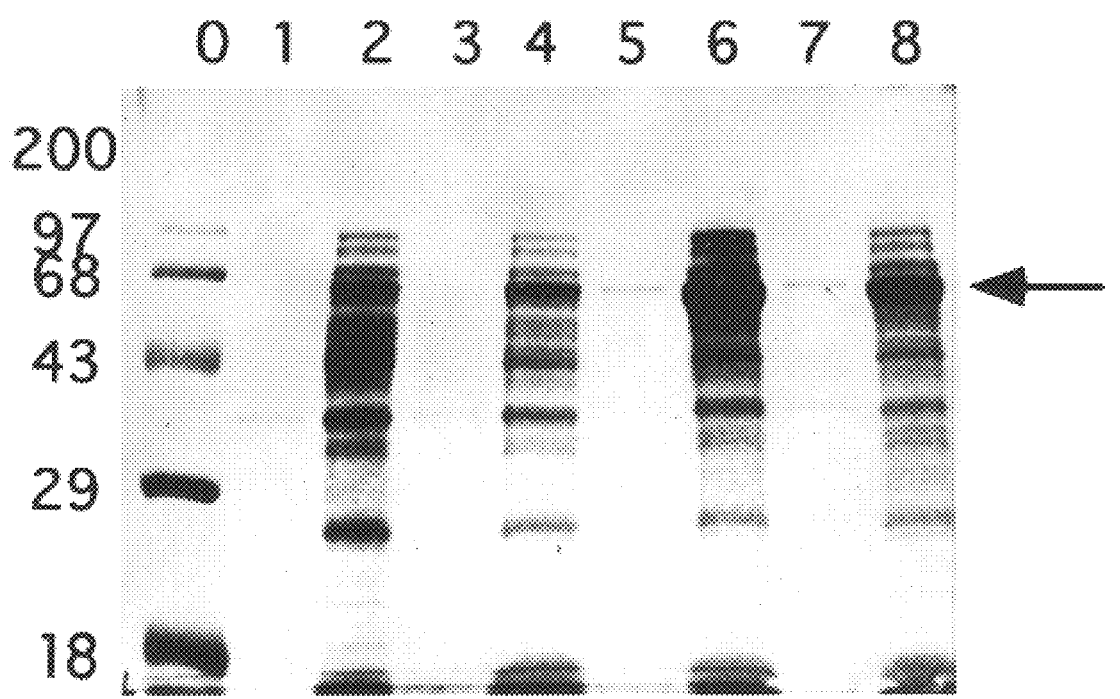

FIG. 11 depicts a Coomassie gel of the expression of PelB and OmpT NucA fusion proteins. Lane 0—Prestained high molecular weight protein standards with apparent molecular weights as shown in the Figure; Lanes 1, 3, 5 & 7—samples of the supernatant; Lanes 2, 4, 6 & 8—samples of the cell pellet; Lanes 1–4—from BL21(DE3)pLysS/pPX707 (OmpT-NucA); Lanes 5–8—from BL21(DE3)pLysS/ pPX708 (PelB-NucA). The arrow shows the migration of NUcA.

Figure 12:
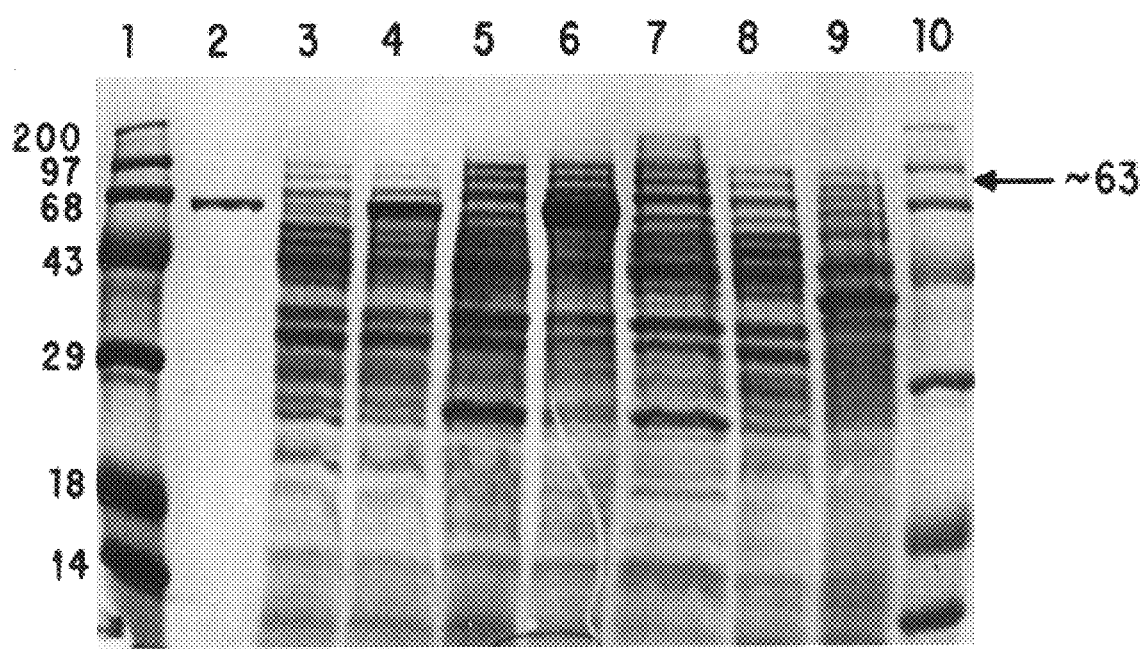

FIG. 12 depicts a Coomassie-stained 12% SDS-PAGE gel on cell lysates from constructs with different signal sequences. Also included is the mature clone pPX709 with an optimized TIR, and the NTHi P860295 lysate. A negative control is the induced vector (pTrcHisC) alone. Here the vector does not contain any NucA sequence. Lanes 1 and 10—molecular weight standards as above; Lane 2—purified prep of rNucA from pPX691; Lane 3—uninduced lysate from pPX691; Lane 4—induced lysate from pPX691; Lane 5—induced lysate from pPX707; Lane 6—induced lysate from pPX708; Lane 7—induced lysate from pPX709; Lane 8—lysate from P860295; Lane 9—induced pTrcHisC.

Figure 13:
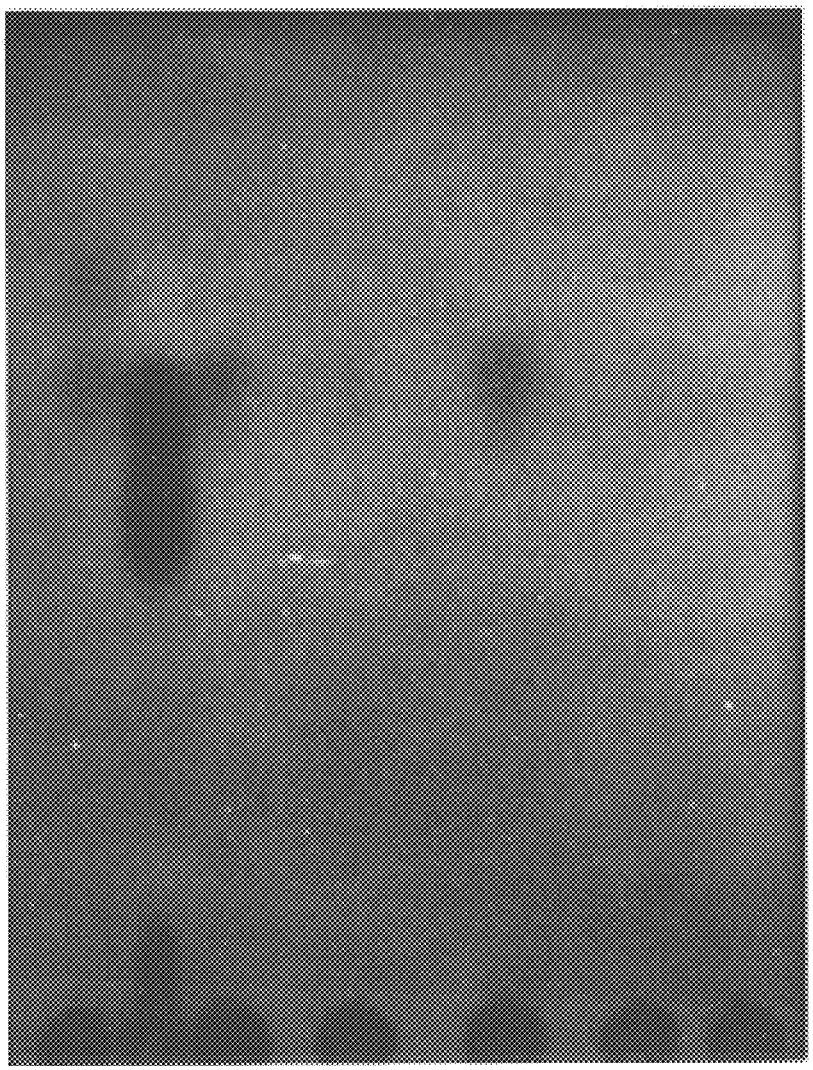

FIG. 13 depicts the results of a 5'-nucleotidase assay on a TLC plate. Nucleotidase activity was determined with whole cells and purified native or recombinant NucA protein. The reactions contained the following additions: Lane 1: 10 μl P860295 cells; Lane 2: 5 μl rNucA; Lane 3: 1 μl rNucA; Lane 4: 5 μL nNucA; Lane 5: 1 μl nNucA; Lane 6: no added nucleotidase; Lane C: 1 μl of 21.5 mM adenosine plus 1 μl of reaction from lane 6 (control for migration of adenosine shown as A). Solvent front shown.

Figure 14:
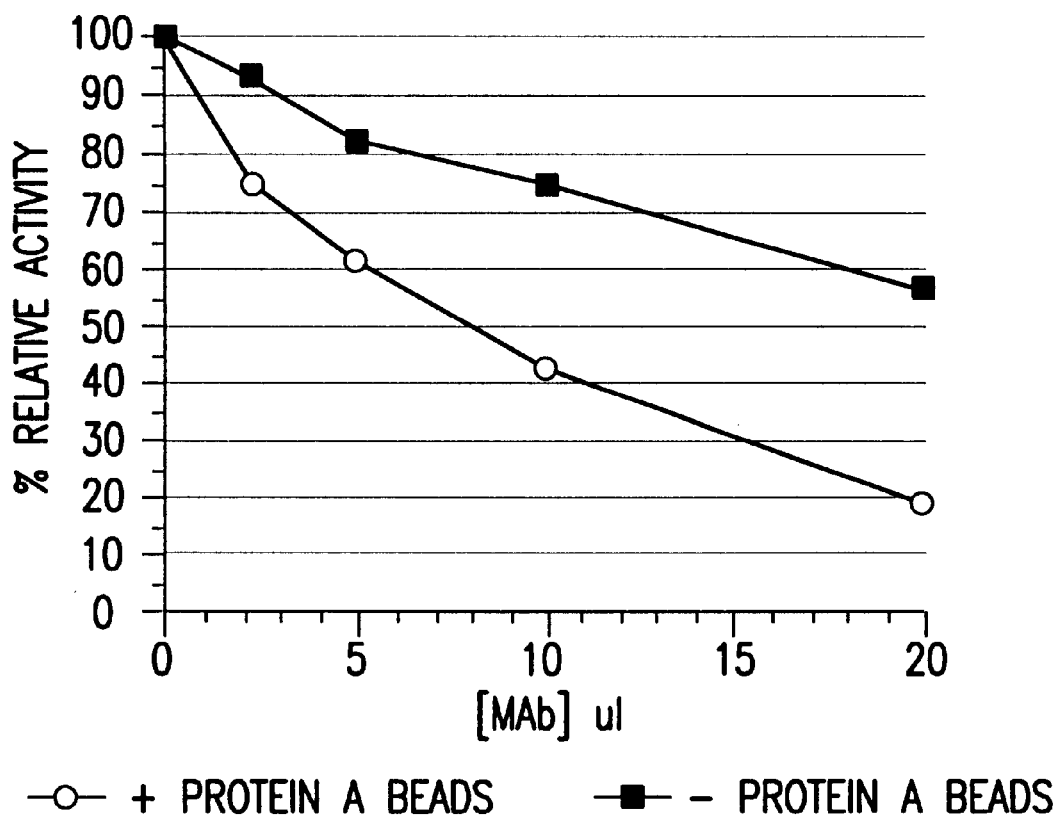

FIG. 14 depicts the inhibition of rNucA(pPX691) 5'-nucleotidase activity by the antin-NucA Mab Nt-63-34-25. The inhibition of enzymatic activity is depicted in the absence (solid squares) or presence (hollow circles) of Protein A beads.

Figure 15:
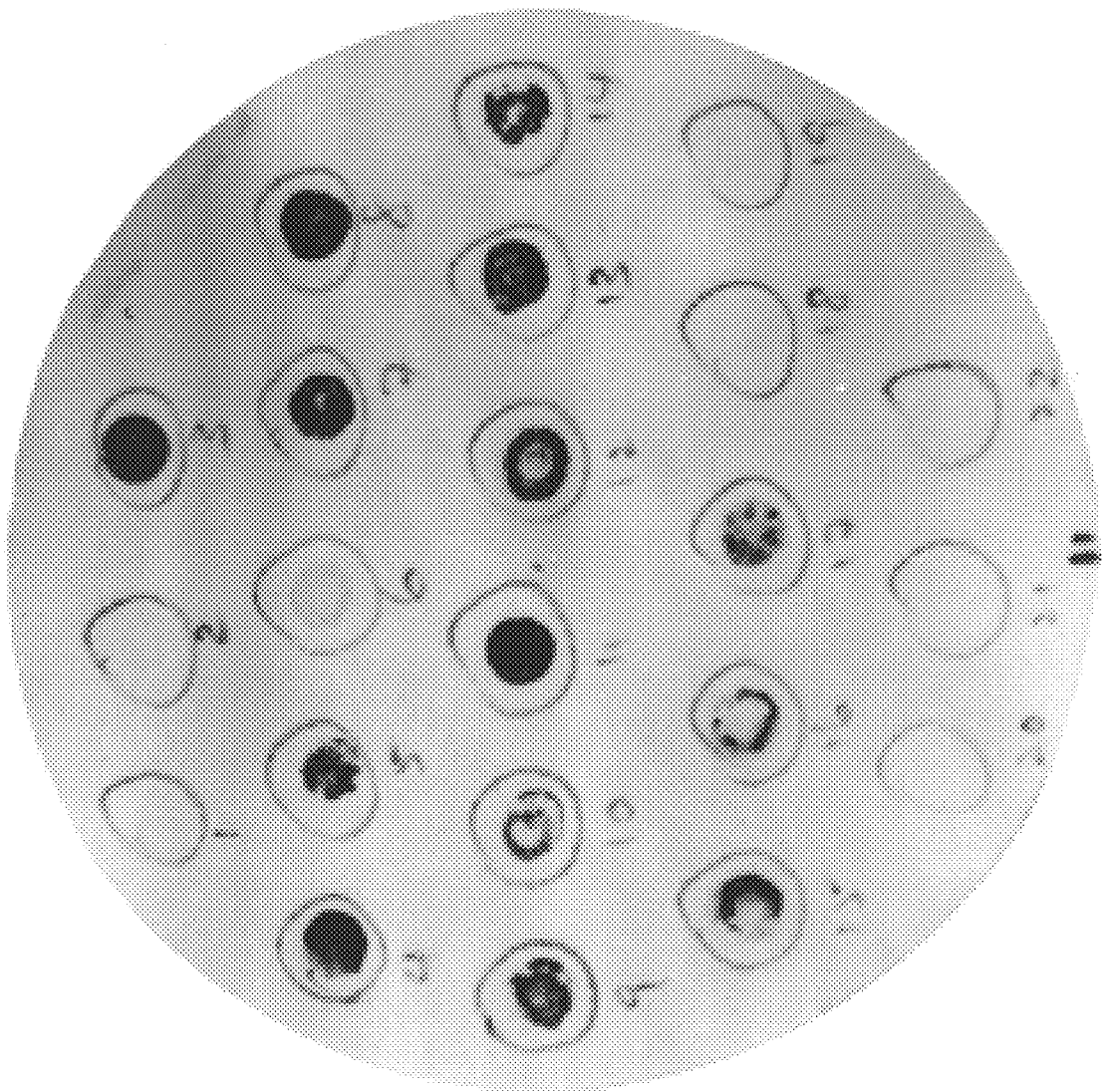

FIG. 15 depicts the Dot blot hybridization of several NTHi and type b, Eagan strain, as well as other species, probed with a nucA 420 bp dig-labelled probe. Numbers 1–22 are as set forth in Example 8 below.

DETAILED DESCRIPTION OF THE INVENTION

This invention relates to an isolated and purified H. influenzae NucA protein. The NucA protein has the amino acid sequence of amino acids 1–603 of SEQ ID NO:2. Amino acids 1–25 comprise the signal peptide. After normal processing, the mature NucA protein has the amino acid sequence of amino acids 26–603 of SEQ ID NO:2. The NucA protein has a molecular weight of approximately 63,000 Daltons (63 kD) as measured on a 12% SDS-PAGE gel. The NucA protein also has 5'-nucleotidase activity (see Example 5) which is inhibited by an anti-native NucA monoclonal antibody (Example 6).

The NucA protein is present in very small amounts on the cell surface of *H. influenzae*. NucA is a membrane associated protein. This protein is highly conserved among all the *H. influenzae* strains tested. The invention relates further to peptides of NucA protein comprising an epitope or epitopes thereof. Such peptides incorporate one or more epitopes that are immunologically cross-reactive with one or more epitopes of the NucA protein. Such peptides are first generated and then tested for cross-reactivity.

The NucA protein is obtained by isolation from the *H. influenzae* organism, by recombinant DNA expression or by chemical synthesis. Chemical synthesis involves using standard chemistries for solid and liquid phase synthesis, particularly for production of peptides of NucA protein comprising an epitope or epitopes thereof.

A method for the isolation of the NucA protein from the *H. influenzae* organism is detailed in Example 1 below. In summary, the organism is extracted with KSCN, the extract is passaged through two hydroxylapatite columns and subjected to SDS-PAGE. The band at 63 kD on the gel is cut out to obtain purified NucA protein. Example 4 details two alternative purification methods. The second hydroxylapatite column may be replaced by a MonoQ column. Alternatively, the KSCN extraction step is replaced by a NaCl extraction step.

Cloning of the gene encoding the NucA protein was not straightforward. Example 2 below sets forth the several strategies which were tried unsuccessfully, as well as the eventual successful cloning of the nucA gene containing the DNA sequence encoding the NucA protein. Successful cloning was followed by the expression of the NucA protein and sequencing of the nucA gene. The complete nucA gene sequence is set forth in SEQ ID NO:1, nucleotides 229–2037. The signal peptide is encoded by nucleotides 229–303. The mature NucA protein is encoded by nucleotides 304–2037.

Example 3 below details the expression of the NucA protein. The full length nucA gene was cloned into an *E. coli* expression vector, pTrcHisC, and designated pPX691. The nucA gene was expressed in *E. coli* as a mature NucA protein with its signal sequence processed. A culture was induced with IPTG for expression of the NucA protein. Expression was confirmed by both Western analysis and Coomassie gel analysis.

This invention further relates to an isolated and purified DNA sequence comprising a DNA sequence encoding the NucA protein of *H. influenzae*, as well as to concomitant DNA sequences which encode peptides of NucA protein comprising an epitope or epitopes thereof.

A variety of host cell-vector systems are used to express the NucA protein and peptides of this invention in addition to those detailed in Example 3. The vector system is compatible with the host cell used. Suitable host cells include bacteria transformed with plasmid DNA, cosmid DNA or bacteriophage DNA; viruses such as vaccinia virus and adenovirus; yeast such as Pichia cells; insect cells such as Sf9 or Sf21 cells; or mammalian cell lines such as Chinese hamster ovary cells; as well as other conventional organisms.

A variety of conventional transcriptional and translational elements can be used for the host cell-vector system. The nucA DNA is inserted into an expression system and the promoter and other control elements are ligated into specific sites within the vector, so that when the plasmid vector is inserted into a host cell, the nucA DNA can be expressed by the host cell.

Heterologous signal peptides are used in order to translocate the recombinant NucA protein across the cellular membrane. Example 3 details the separate cloning upstream of the mature nucA gene of the OmpT and PelB signal sequences. Expression of the NucA protein was successful with each of these signal sequences.

The plasmid is introduced into the host cell by transformation, transduction or transfection, depending on the host cell-vector system used. The host cell is then cultured under conditions which permit expression of the NucA protein by the host cell.

In addition to the the DNA sequence obtained from NTHi strain P860295 which encodes the NucA protein (SEQ ID NO:1), the present invention further comprises DNA sequences which, by virtue of the redundancy of the genetic code, are biologically equivalent to the sequences which encode for the NucA protein, that is, these other DNA sequences are characterized by nucleotide sequences which differ from those set forth herein, but which encode a protein or peptides having the same amino acid sequences as those encoded by the DNA sequence of SEQ ID NO:1.

In particular, the invention contemplates those DNA sequences which are sufficiently duplicative of the sequence of SEQ ID NO:1 so as to permit hybridization therewith under standard high stringency Southern hybridization conditions, such as those described in Sambrook et al. (3), as well as the biologically active enzymes produced thereby.

This invention also comprises DNA sequences which encode amino acid sequences which differ from those of the NucA protein, but which are biologically equivalent to those described for that protein (SEQ ID NO:2). Such amino acid sequences may be said to be biologically equivalent to those of the NucA protein if their sequences differ only by minor deletions from or conservative substitutions to the NucA sequence, such that the tertiary configurations of the sequences are essentially unchanged from those of the NucA protein.

For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Nucleotide changes which result in alteration of the N-terminal or C-terminal portions of the protein molecule would also not be expected to alter the activity of the protein. Each of the proposed modifications is well within the routine skill in the art, as is determination of retention of biological activity of the encoded products. Therefore, where the terms "nucA DNA" or "NucA protein" are used in either the specification or the claims, each will be understood to encompass all such modifications and variations which result in the production of a biologically equivalent protein.

Specifically, as set forth in Example 9 below, the NucA protein of this invention may have one or more of the following changes to the amino acid sequence of SEQ ID NO:2: K79E, N186K, S262G, V294A, E305Q, K327R, T337A, D360Y, R376H or V436I. One or more of these amino acid changes are present in other NTHi genomes and the type b, Eagan strain.

The NucA protein and peptides of NucA protein comprising an epitope or epitopes thereof are useful in the preparation of vaccines to confer protection to warm-blooded animals against otitis media and pneumonia caused by *H. influenzae*.

These vaccine compositions comprise an isolated and purified NucA protein of *H. influenzae* or a peptide of NucA protein comprising an epitope or epitopes thereof, wherein the vaccine composition elicits a protective immune response in a mammalian host.

Vaccines containing the NucA protein or peptides may be mixed with immunologically acceptable diluents or carriers in a conventional manner to prepare injectable liquid solutions or suspensions. In addition, the vaccines may include aluminum hydroxide, aluminum phosphate (alum) or other pharmaceutically acceptable adjuvants, such as Stimulon™ QS-21 (Cambridge Biotech Corporation, Worcester, Mass.), MPL™ (3-O-deacylated monophosphoryl lipid A; RIBI ImmunoChem Research, Inc., Hamilton, Mont.), and IL-12 (Genetics Institute, Cambridge, Mass.).

The vaccines of this invention may also include additional *H. influenzae* proteins which are well-known in the art. Examples of such proteins are those designated P6 and P4 (the latter is also known as protein "e").

The vaccines of this invention are administered by injection in a conventional manner, such as subcutaneous, intraperitoneal or intramuscular injection into warm-blooded animals, as well as by oral administration and intranasal administration, to induce an active immune response for protection against otitis media caused by NTHi. The dosage to be administered is determined by means known to those skilled in the art. Protection may be conferred by a single dose of vaccine, or may require the administration of several booster doses.

Normally, in the absence of human clinical data, active immunization in a recognized animal model is relied upon to predict the efficacy of a vaccine in humans. It has been proposed that the chinchilla provides an animal model for active immunization against NTHi (4).

However, later active immunization experiments with candidate NTHi proteins demonstrated that the chinchilla is not an acceptable model (unpublished data, Lederle-Praxis Biologicals, West Henrietta, N.Y.).

The accepted animal model for Hib consists of passive immunization of infant rats (5) together with in vitro bactericidal assays (6). Active immunization is not possible with the infant rat. The infant rat is susceptible to Hib for only 4–5 days; thereafter it is not susceptible. Due to this brief time period, it is not possible to actively immunize the infant rat, because the challenge with the bacterium would have to take place more than five days after immunization and the animal does not respond to challenge at that time. Therefore, passive immunization with the infant rat provides the only feasible animal model for Haemophilus, when taken together with bactericidal assay data.

In the present invention, the NucA protein is shown to be a viable vaccine candidate by reason of its activity in both infant rat passive immunization studies and bactericidal assays (as detailed in Example 7 below). In that infant rat study, type b Eagan was used as the challenge strain. The results demonstrated a reduction in bacteremia in rats passively immunized with anti-recombinant NucA protein serum.

In addition to the foregoing modes of vaccine administration, a technique variously known as genetic immunization, polynucleotide immunization or naked DNA technology may be used. Immunization with DNA has been used to protect animals from challenge with Influenzae A (7). In this technique, the nucA DNA is used in forms such as plasmid DNA and naked DNA, and is administered to the mammalian host in a variety of ways, including parenterally, mucosally and by gene gun inoculation, as described for example by Fynan et al. (8). Facilitating agents such as bupivicaine may be used in this technique.

The nucA DNA is also used to generate probes for use as a diagnostic in the detection of *H. influenzae* in selected clinical samples or laboratory strains. Clinical samples which are analyzed include clinical isolates, otic isolates and throat cultures. The probes are used in the diagnosis of meningitis, otitis media and pneumonia caused by Hib and NTHi, respectively.

One such probe is the 420 bp probe spanning nucleotides 416–835 of SEQ ID NO:1. As described in Example 8 below, this 420 bp probe was used in a dot blot hybridization assay. The probe was positive for all Haemophilus strains tested, including all NTHi strains and type b, Eagan strain. The probe was negative for other bacterial strains, including *E. coli, Neisseria gonorrhoeae, Helicobacter pylori, Moraxella catarrhalis* and *Salmonella typhimurium*. As expected, the probe was positive for an *E. coli* strain containing a rnucA plasmid. Thus, nucA probes are specific for nucA sequences and are useful for the diagnosis of the presence of *H. influenzae* strains.

Samples of the *E. coli* strain InvαF' harboring the recombinant plasmid pPX691 were deposited by Applicants with the American Type Culture Collection, 12301 Parklawn Drive, Rockville, Md. 20852, U.S.A., and have been assigned ATCC accession number 98104. The plasmid pPX691 contains a nucA insert encoding the NucA protein having the amino acid sequence of residues 26–603 of SEQ ID NO:2.

The material deposited with the ATCC can also be used in conjunction with conventional genetic engineering technology to generate biologically equivalent sequences to the NucA protein, including but not limited to those wherein the amino acid sequence of amino acids 26–603 of SEQ ID NO:2 is modified by one or more of the following amino acid residue changes selected from the group consisting of K79E, N186K, S262G, V294A, E305Q, K327R, T337A, D360Y, R376H or V436I.

In order that this invention may be better understood, the following examples are set forth. The examples are for the purpose of illustration only and are not to be construed as limiting the scope of the invention.

EXAMPLES

The following *H. influenzae* strains were used:

| NTHi Strains | |
|---|---|
| P860295 | Otic isolate from Children's Hospital, Pittsburgh, PA |
| P810384 | Otic isolate from Children's Hospital, Pittsburgh, PA |
| P810568 | Clinical isolate from Children's Hospital, Pittsburgh, PA |
| P861454 | Throat culture from Children's Hospital, Pittsburgh, PA |
| P880859 | Otic isolate from Children's Hospital, Pittsburgh, PA |
| N1955 | Clinical isolate from University of Texas Southwestern Medical Center at Dallas |
| TN106 | Clinical isolate frozn University of Texas Southwestern Medical Center at Dallas |
| SH1013 | Ear isolate froxn Texas |

-continued

| NTHi Strains | |
|---|---|
| SH1014 | Ear isolate from Ohio |
| SH1015 | Blood isolate from Texas |
| DL208 | Clinical isolate from University of Texas Southwestern Medical Center at Dallas |
| N830161E | Clinical isolate from University of Texas Southwestern Medical Center at Dallas |
| H305 | Clinical isolate from Pittsburgh, PA |
| Type b | |
| Eagan | American Type Culture Collection, e.g., ATCC 31,441 or 53,763 |
| Whittier | Unencapsulated type b from Children's Hospital, Boston, MA |

Standard molecular biology techniques are utilized according to the protocols described in Sambrook et al. (3).

Example 1

Identification Of NucA Protein

All the NTHi strains and the type b Eagan and Whittier strains were grown in BHI (Brain Heart Infusion) broth, supplemented with 10 µg/ml hemin stock (0.1 µg hemin-0.1 µg histidine-4 ml triethanolamine per 100 ml solution) and 40 µg/ml NAD or with 2% Fildes enrichment (Remel, Lenexa, Kans.) and 20 µg/ml NAD. Cultures were incubated at 37° C. with shaking.

Figure 1:
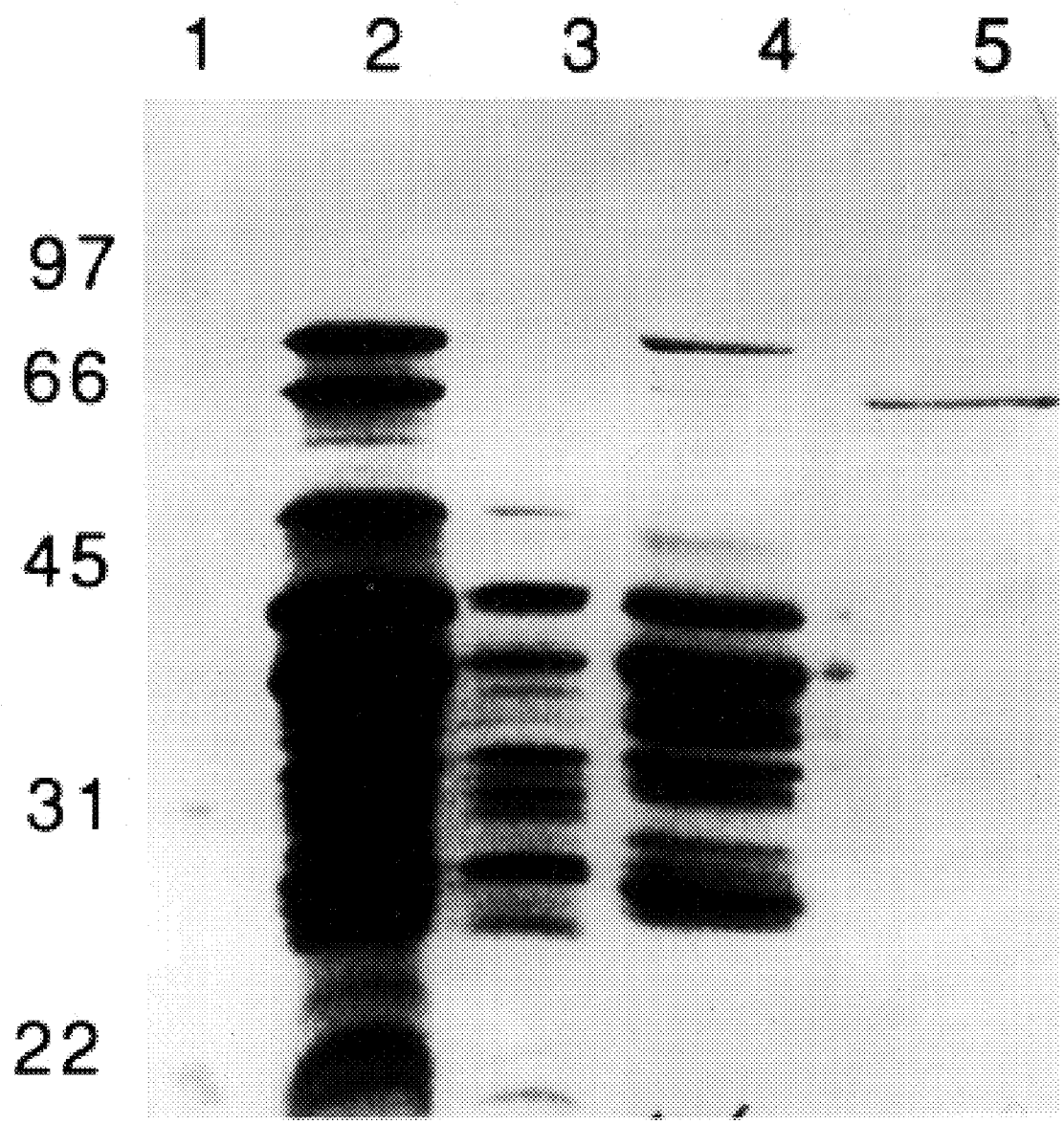
FIG. 1 depicts the KSCN extract of NTHi strain P860295 and its eluates from a Bio-Gel™ HT hydroxylapatite column run on a 12% SDS-PAGE gel. Lane 1—BioRad's low molecular weight standards (apparent molecular weights of 97, 66, 45, 31 and 22 kD); Lane 2—pre-column 3M KSCN extract; Lane 3—column flowthrough; Lane 4—0.3M NaPO$_4$, pH 7.0, eluate; Lane 5—0.4M NaPO$_4$, pH 7.0, eluate.

A cell culture from NTHi strain P860295 was pelleted, washed with PBS or saline and resuspended in 10 ml of 3M KSCN-0.1M $PO_4$, pH 6.0, per liter of culture and rocked at room temperature (RT) for 30 minutes. Unique bands (different than the outer membrane proteins (OMPs)) were seen when the KSCN extract was run on a 12% SDS-PAGE gel. One of these proteins ran at about 63 kD (see FIG. 1) and was further purified as described below.

The KSCN extract was clarified by centrifugation in the Sorvall centrifuge at 8000 rpm for 20 minutes, then at 10,000 rpm for 15 minutes in an SS-34 rotor. The supernatant was passed through a 0.22 µm filter and dialyzed against two changes of two liters each of 0.05M sodium phosphate, pH 7.0. Dialyzed extract was loaded onto a Bio-GelTM HT hydroxylapatite (HA) column (0.2–0.3 ml HA per ml extract) and equilibrated with 0.05M phosphate, pH 7.0. The column was washed with about 10 column volumes of 0.05M phosphate, pH 7.0. The 63 kD protein was step eluted with about 5–6 column volumes of 0.3M phosphate, pH 7.0, followed by a similar volume of 0.4M phosphate, pH 7.0. The fractions containing the protein were pooled and concentrated in an Amicon stir cell using the YM30 membrane and particulate matter was pelleted at 3000 rpm for 10 minutes. The supernatant was dialyzed against 0.05M phosphate, pH 7.0, for further purification over a second HA column (about half the volume of the first column), and equilibrated with 0.05M phosphate, pH 7.0. After the sample was loaded, the column was washed first with 0.05M phosphate, pH 7.0, then 0.3M phosphate, pH 7.0 (about 2 column volumes). The protein was eluted with a 0.3M–0.4M phosphate, pH 7.0 gradient (about 3 column volumes). Fractions were collected and all those containing the essentially pure 63 kD band (identified on the basis of size by an SDS-PAGE gel), were pooled and concentrated.

Figure 2:
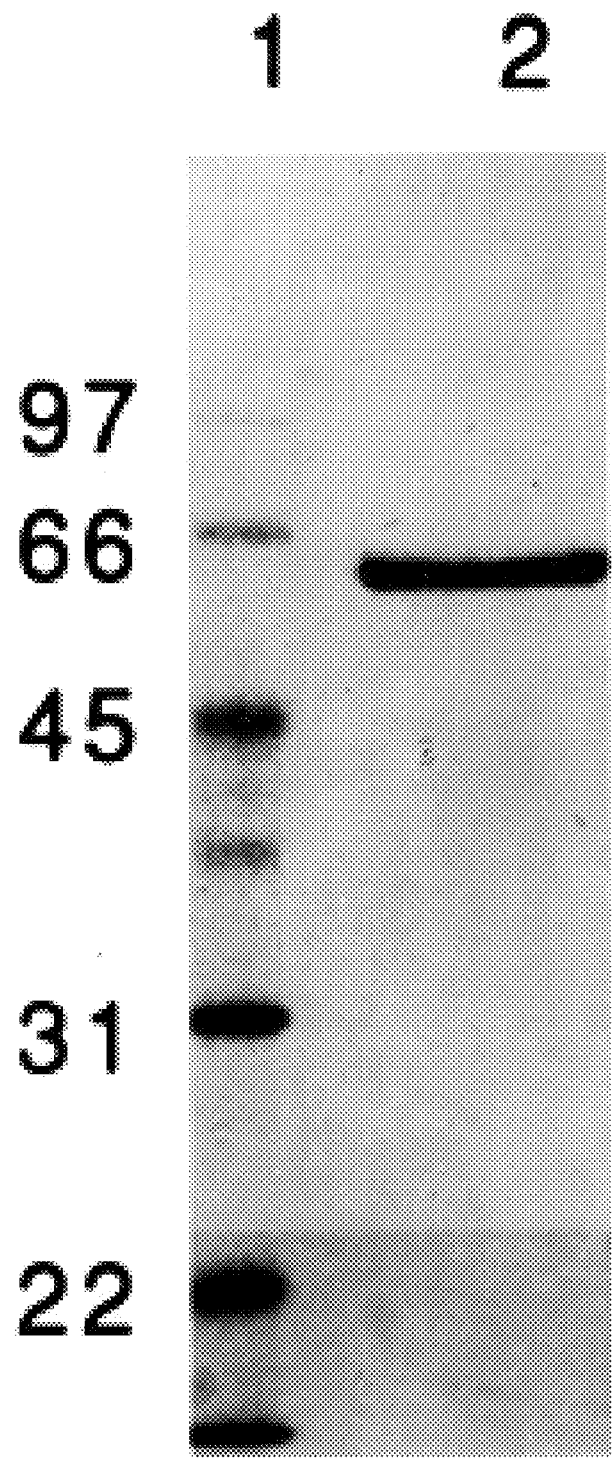
FIG. 2 depicts a 12% SDS-PAGE gel of the further purified NucA protein, showing it to be approximately 63 kD. Lane 1—BioRad's low molecular weight standards (same as in FIG. 1); Lane 2—concentrated NucA before ethanol precipitation.

Finally, 100 µg protein eluted from a third HA column was repeatedly ultrafiltered in a Centricon 30 to replace the phosphate with sterile water, ethanol precipitated and subjected to SDS-PAGE (see FIG. 2). Concentration was determined by the Peterson-Lowry method and N-terminal amino acid sequencing analysis was performed. The first 26 amino-terminal residues have the sequence set forth in residues 26–51 of SEQ ID NO:2. Purification to homogeneity was accomplished by electrophoresing the protein on a gel and then cutting out the 63 kD band. The protein was electoeluted from the gel slice, ethanol precipitated, quantitated, checked on an SDS-PAGE and used in immunogenicity study #1. See Example 7 below.

An animal study (study #1) was performed to determine the immunogenicity of NucA protein. See Tables 3, 5, and 6 below for the animal study data. Antibody titers to this protein were measured. Whole cell (WC) and bactericidal (BC) assays were determined on the sera. The native protein, designated "NucA", was found to be antigenic and cross-reactive among all strains tested in WC enzyme-linked immunosorbent assays (ELISA). In addition, the sera had bactericidal activity for two out of four heterologous strains tested. Therefore, the NucA protein was considered to be a potential vaccine candidate. In order to generate larger quantities of the NucA protein, the gene encoding the protein would first have to be identified and cloned in order to be expressed recombinantly.

Example 2

Cloning Of The nucA Gene

Preliminary Steps

In carrying out this work, the following reagents and strains were used: DNA modifying enzymes from New England Biolabs (Beverly, Mass.) or Boehringer Mannheim (Indianapolis, Ind.); agarose LE from Boehringer Mannheim; Sea Plaque™ low melting temperature agarose from FMC (Rockland, Me.); adenosine 5'-monophosphate and adenosine from Sigma (St. Louis, Mo.); Si250F TLC plates from J.T. Baker Chemical Co. (Phillipsburg, N.J.); TA Cloning kit, INVαF', and pRSETC and pTrcHisC expression vectors from Invitrogen (San Diego, Calif.); BL21 (DE3)pLysS, pET12a, and pET20b from Novagen (Madison, Wis.); the λ Zap™II vector and XL1-Blue MRF' host strain from Stratagene (LaJolla, Calif.).

Standard molecular biology methods used were similar to those reported by Sambrook et al. (3).

All the NTHi strains and the type b Eagan and Whittier strains were grown in BHI (Brain Heart Infusion) broth, supplemented with 10 µg/ml hemin stock (0.1 g hemin-0.1 g histidine-4 ml triethanolamine per 100 ml solution) and 40 µg/ml NAD, or with 2% Fildes enrichment and 20 µg/ml NAD. Cultures were incubated at 37° C. with shaking.

Construction Of A P860295 Library In A λ Zap™II Vector

Approximately 50 µg (100 µl) of P860295 chromosomal DNA was digested with 20 units Tsp509I restriction enzyme (New England Biolabs [NEB]) in 10× buffer 4 (NEB) at 65° C. for 50 minutes. Fragments (4–10 kb) were gel isolated on a 0.7% Sea Plaque (FMC) agarose gel run at 40 V for about 14 hours. The appropriate size bands were cut out of the gel, melted at 70° C., diluted with one volume of 1× TE, pH 7.5, and extracted with an equal volume of warm (RT-37° C.) phenol. The supernatant was chloroform extracted to remove phenol, one-tenth volume 3M sodium acetate added and the DNA precipitated with two volumes of cold absolute ethanol. DNA was pelleted, washed in 70% ethanol, dried and resuspended in 10 µl sterile water. Different amounts of DNA were ligated to EcoRI digested and dephosphorylated λ Zap™II vector arms (Stratagene) at 12° C. overnight. The λ Zap™II vector has been designed to allow in vivo excision and recircularization of cloned inserts contained within the vector to form a phagemid containing the cloned insert. Ligations were packaged using Stratagene's extracts and plated on XL1 Blue MRF' cells. Efficiency of insertion varied from 90% to 95% based on white versus blue plaques on X-gal (5-bromo-4-chloro-3-indolyl-β-D-galactopyranoside) plates. The white plaques contained inserts of about 4–6 kb.

Plaques from the library were screened with monoclonal and polyclonal antibodies, or with DNA probes, either by hybridization with digoxigenin-11-dUTP (dig-dUTP) probes (Boehringer Mannheim), or in PCR reactions (see below).

Immunoblot screening Of The λ Zap™II Library

The A plaques were plated, about 500 pfu, onto 100 mm TY (5 g NaCl, 2 g MgSO₄.7H₂O, 5 g yeast extract, 10 g Tryptone, per liter broth adjusted to pH 7.5 with NaOH, plus 15 g Difco agar) plus isopropyl-beta-D-thiogalactopyranoside (IPTG) plates and incubated at 37° C. overnight. The plates were chilled at 4° C. for at least two hours. The plaques were blotted with dry Schleicher & Schuell (Keene, N.H.) NC™ nitrocellulose membranes for 5–10 minutes. The filter was blocked in 15 ml 5% BLOTTO (in 1XPBS) in 100 mm petri dish. Tween™-20 (0.1–0.3%) was sometimes added to reduce background at 0.1–0.3%. The filter was rocked at RT for 4–6 hours or at 37° C. for one hour. The BLOTTO was removed and primary antibody in 5% BLOTTO was incubated with the filter at 4° C. overnight. The primary antibodies used were monoclonal antibodies Nt63-34-25, Nt63-60-14, Nt63/2-1-45, and Nt63/2-13-42 (generated as described in Example 7), or a mix of these four monoclonal antibodies, or polyclonal rabbit serum that had been absorbed to XL1-Blue MRF', Y1090R⁻, Y1089R⁻ and Y1088 cell cultures and λ Zap™II lysate. Washes were done at RT with 15 ml 5% BLOTTO for 5–10 minutes each, repeated three times. Then the filter was incubated with secondary antibody (KPL anti-mouse IgG+M #QJ08-1, phosphatase conjugated) diluted 1:1000 in 5% BLOTTO±0.1–0.3% Tween™-20 and rocked for one hour at RT. Again, the filter was washed 3x with 15 ml each of 1XPBS+0.1–0.3% Tween™-20 at RT for 5–10 minutes. One additional wash was performed in 1x PBS. The filter was then equilibrated in developing buffer (0.1M Tris, pH 9.5, 0.1M NaCl, 5 mM MgCl₂) for five minutes at RT. The filter was then placed in petri dish containing 10 ml developing buffer plus 45 µl NBT (nitro blue tetrazolium) and 35 µl BCIP (5-bromo-4-chloro-3-indolyl phosphate), and rocked to make sure the filter was immersed in developer. It was then kept in the dark on a flat surface until spots were sufficiently dark. The reaction was stopped by rinsing the filter in deionized water several times and dried on 3 MM Whatman paper in the dark.

There seemed to be a problem with high background reactivity to λ Zap™II plaques. The secondary antibody was found to be the major cause of the background binding. Goat anti-mouse IgG+M lot # QJ08-1 (Kirkegaard & Perry Labs, Gaithersburg, Md.), alkaline phosphatase conjugated, had the lowest background when used at 1:1000 dilution, among those tested. Immunoblot screening did not yield any positive clones for NucA. Because of the background nonspecific binding, further work in this direction did not appear promising. Therefore, another strategy was employed to try to pull out nucA clones and sequence.

Plaque Hybridization On λ Zap™II Library

Two 24-mer degenerate oligonucleotide probes were designed from the N-terminal sequence of the NucA protein (see Example 4 below) and utilizing a *H. influenzae* codon usage table compiled for this purpose. The probes encompass amino acids 1–8 and 14–21 of the N-terminus of the mature protein, and were named P1 and P2 respectively:

```
P1    AAAGAAGCACCACAAGCACATAAA     (SEQ ID NO:3)

P2    ATTTTACATATTAATGATCATCAT     (SEQ ID NO:4)
```

P1 and P2 were each wobbled at four bases. For P1, the A at residue 9 may be a T, the A at residue 12 may be a T, the A at residue 18 may be a T, and the T at residue 21 may be a C. For P2, the T at residue 3 may be a C, the T at residue 9 may be a C, the T at residue 12 may be a C, and the T at residue 21 may be a C. The primer P1 corresponds to nucleotides 304–327 of SEQ ID NO:1, except that the G at nucleotide 309 is an A in this primer. The primer P2 corresponds to nucleotides 343–366 of SEQ ID NO:1, except that the G at nucleotide 348 is an A in this primer. The oligos were 3'-end labelled with dig-dUTP according to the supplier's recommendations.

The P1 and P2 probes were checked with genomic DNA by Southern hybridizations on EcoRI and BamHI digested P860295 chromosomal DNA and EcoRI digested XL1-BlueMRF' chromosomal DNA. With P860295 DNA, only one band was seen with the P1 probe at approximately 4 kb in the EcoRI digest, whereas two bands were seen with the P2 probe at approximately 4 kb and 1.8 kb. The BamHI digest of P860295 DNA showed an approximately 30 kb band. XL1-BlueMRF' DNA did not cross-react with the probes. Prehybridization and hybridization incubations with P1 as the probe were performed at 53° C.; for the P2 probe, they were performed at 45° C. Washes for P1 hybridization were performed at 48° C.; washes for P2 were performed at 40° C. following standard protocols.

Plaque lifts were performed according to the method in the Hybond-N (Amersham) protocol booklet. Prehybridization and hybridization were performed at 42° C., while washes were performed at 45° C. for P1 and 38° C. for P2. Ten plates of library lysate, about 1000 pfu per 100 mm plate, were screened using P1 or P2 as probes. Six putative positives were picked, five from filter #9 (P2 probe) and one from filter #5 (P1 probe). These were saved and further screened by PCR. See below in PCR screening section. Phage library DNA purification—Approximately 5 ml of P860295 λ Zap™ library phage were purified through a glycerol step gradient (9). The phage DNA was resuspended with 20 µL TE (10 mM Tris-HCl, pH 8.0, 1 mM EDTA) at approximately 1 ng/µL.

DNA purification—DNAs were purified either directly or from agarose gels using the LiCl protocol (10) or the GeneClean kit (Bio 101 Inc.) as described by the manufacturer. Plasmid mini prep DNAs were isolated from 1mL overnight cultures using the Wizard mini plasmid DNA kit (Promega) or standard alkaline lysis-phenol extraction methods. Large scale plasmid DNA was isolated from 100–500 mL overnight cultures using the Qiagen maxi plasmid DNA kit (QIAGEN Inc.).

Figure 3:
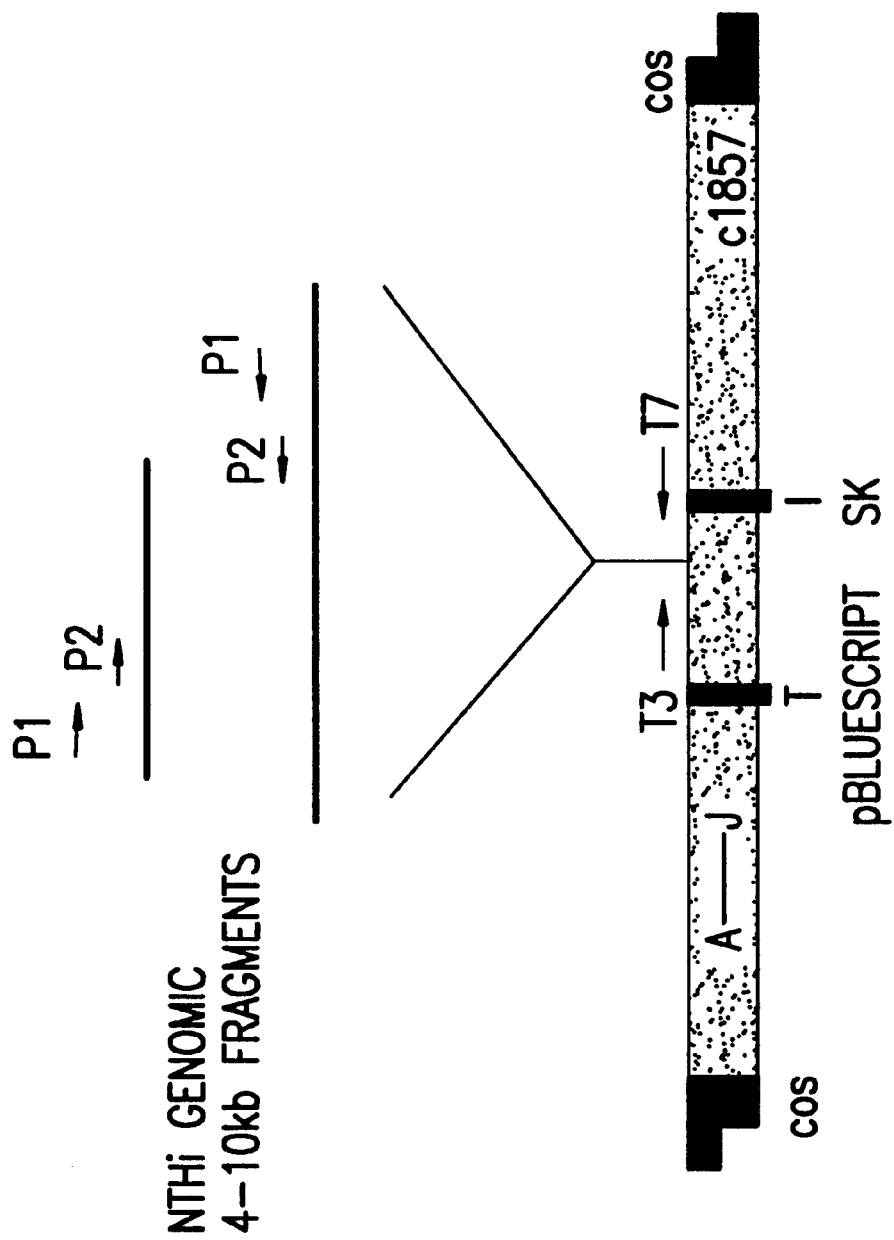
FIG. 3 depicts proposed nucA specific PCR products amplified from the NTHi λ Zap Library. The schematic of the λ Zap Library shows the insertion site of P860295 genomic DNA fragments into the pBluescript™ region of the ™ Zap™II phage, and the relative orientation of the nucA specific degenerate primers, P1 and P2, on potential genomic DNA fragments containing these sites. The phage specific T3 and T7 primer sites are shown fixed on the λ Zap™II DNA.

Partial DNA sequence of nucA—The rationale for doing the following experiment was two-fold: (1) The NTHi λ Zap™II library was constructed from a partial Tsp509I genomic digest, therefore, discrete size PCR bands should be generated by amplifying the NTHi λ Zap™II library using combinations of the phage specific primers T3 (SEQ ID NO:16) and T7 (SEQ ID NO:8) and nucA specific primers P1 (SEQ ID NO:3) and P2 (SEQ ID NO:4) as illustrated in FIG. 3; and (2) PCR can be made to be less stringent and therefore more tolerant of nucleotide mismatches with annealing of the primers. Primer T3 has the following sequence (which does not correspond to nucA):

T3    ATTAACCCTCACTAAAGGGA    (SEQ ID NO:16)

Two DNA amplification reactions were conducted, one with Taq DNA polymerase (Boehringer Mannheim) and the other with PFU DNA polymerase (Stratagene). Amplification cycles were as follows: denaturation, 95° C. for 50 seconds; annealing, 58° C. for 60 seconds; extension, 72° C. for 4 minutes, 30 cycles, and then 72° C. for 10 minutes. An aliquot of the reaction was electrophoresed in an agarose gel. DNA fragments of approximately 2,000 bp and 600 bp were observed using T3+P1 primers and T7+P1 primers, respectively. The primer T7 (SEQ ID NO:8) has the following sequence (which does not correspond to nucA):

T7    CGATCACTATAGGGAGACC    (SEQ ID NO:8)

Both the approximately 600 bp and 2,000 bp DNAs were gel isolated. An attempt was made to reamplify these DNAs, as well as to repeat the previous PCR reaction with NTHi λ Zap™II library DNA. The extension time in the PCR reaction was reduced to two minutes at 72° C. Only the PCR reaction with NTHi λ Zap™II library DNA produced a PCR product, of approximately 600 bp.

The approximately 600 bp amplified DNA was gel isolated, cloned into pCR™II vector using the TA cloning kit as recommended by the supplier (Invitrogen); the resulting plasmid was called pPX640. The DNA sequence of the PCR insert was determined on an ABI 370A DNA sequencer using fluorescent dideoxynucleotide triphosphates, and corresponds to nucleotides 304 to about 840 of SEQ ID NO:1, with two base differences in the wobble positions of the P1 region. Nucleotide 309 is an A and nucleotide 315 is a T. The amino acid sequence deduced from the 5'-end of the insert DNA was identical to the N-terminal protein sequence of the native mature NucA protein, described in Example 1. This confirmed the correct cloning of the partial nucA gene.

Similar PCR bands as above were obtained when the PCR reaction was conducted with the P2 pairs and the annealing temperature was reduced to 48°0 C. An approximately 1.7 kb band was amplified with the T3 primer pair and an approximately 600 bp band was seen with the T7 primer pair. These amplified fragments were similarly cloned into pCR™II vector. Six white colonies were picked from each of P2/T3 and P2/T7 ligations. All had inserts when checked by EcoRI digestion. About 600 bases and approximately 1.7 kb of sequences were obtained from the P1/T7 clone and the P2/T3 clone respectively. The overlap sequences of the two clones were similar, with expected changes in the P2 region because the P2 primer is a degenerate oligonucleotide. The P1/T7 clone contained the 5'-536 bases of nucA and the P2/T3 clone started downstream of P1 and continued for about 1600 bases. The complete upstream and downstream sequences were not included in these clones.

PCR Screening Putative positives from immunoblots (from immunoblot screening of the λ Zap™II library, see above) and oligonucleotide hybridization blots (from plaque hybridization, see above) were subjected to PCR amplification using nucA primers 4101ext and 4102ext, SEQ ID NOS:5 and 6, respectively. These primers were generated during sequencing of the nucA region of pPX640 and have following sequences:

4101ext    CCAAAGTGGATATTGGTG    SEQ ID NO:5
    4102ext    CATCATAGAACTTCACATC    SEQ ID NO:6

The primer 4101ext corresponds to nucleotides 416–433 of SEQ ID NO:1. The primer 4102ext corresponds to the complement of nucleotides 817–835 of SEQ ID NO:1 in the reverse direction.

None of the putative positives from immunoblots or oligonucleotide hybridization gave the predicted 420 bp band when amplified with these two nucA primers.

Generation And Labelling Of The nucA 420 bp probe

Figure 4:
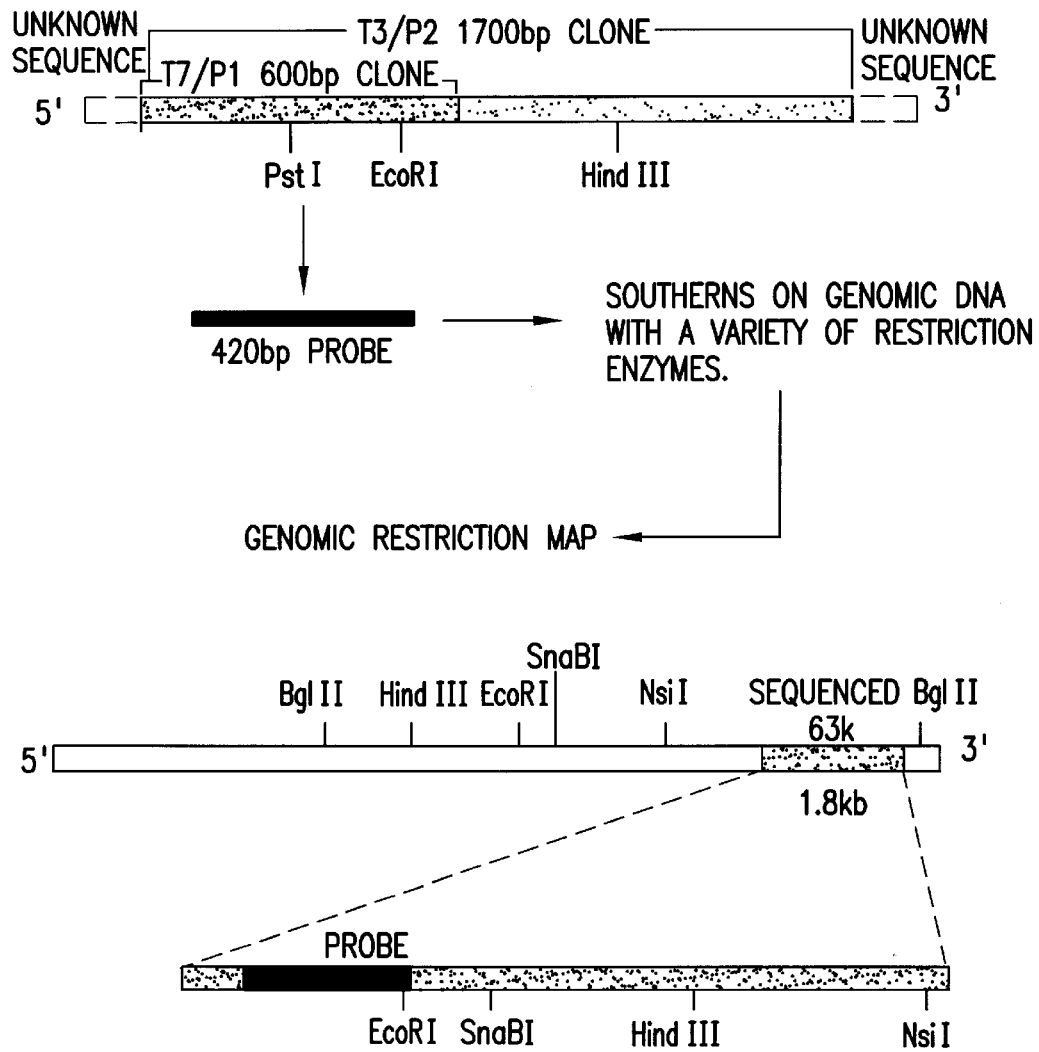
FIG. 4 (top) depicts the two PCR clones which contained most of the mature nucA sequence. From these sequences, a 420 bp probe was constructed that was used in the Southerns on P860295 chromosomal DNA.

The same sequencing primers, 4101ext (SEQ ID NO:5) and 4102ext (SEQ ID NO:6), were used to generate a 420 bp probe (see top of FIG. 4). Initially, the probes were generated from pPX640. Later, all labelled probes were made from P860295 genomic DNA. Use of chromosomal P860295 DNA reduced the background for screening of λ Zap™II clones. The 420 bp probe was dig-dUTP labelled using a mixture of unlabelled nucleotides and varying concentrations of the labelled dig-dUTP nucleotide in a PCR reaction with Tag DNA polymerase (Boehringer Mannheim). Chromosomal P860295 DNA was used as template, which provided a reduced λ Zap™II background. PCR amplification was done for 30 cycles, each run at 95° C. for 30–45 seconds (denaturation step), 42–52° C. for 40–50 seconds (annealing step) and 72° C. for 55–60 seconds (extension step). A hot start was done on the genomic DNA at 95–98° C. for 2–5 minutes. These PCR probes were LiCl-ethanol precipitated and resuspended in 0.1% SDS, in half to equal the original volume, heated at 37° C. for 10 minutes for better resuspension and stored at −20° C. A 1:500–1:1000 dilution of the 420 bp probe was used in hybridization. An estimate of the concentration was done by spotting 1 μl of each dilution, $10^{-2}$ to $10^{-6}$ onto a strip of Hybond-N membrane along with known amounts of labelled standard and matching the intensities after development.

Plaque Hybridization with 420 bp Probe Plaque hybridizations were also conducted using a dig-dUTP labelled 420 bp probe from pPX640 plasmid DNA (see above) according to the manufacturers' recommendations (Hybond-N membrane from Amersham, dig-dUTP for probe labelling from Boehringer Mannheim) and using standard protocols (3). However, this probe produced high background when tested with vector alone (λ Zap™II) plaques. Potential positive plaques from the λ Zap™II library were identified and analyzed, but did not yield the correct size bands in a Southern hybridization experiment.

More library filters and a λ Zap™II control filter were probed with a dig-dUTP labelled 420 bp probe generated from P860295 chromosomal DNA (see above). Two putative positives were identified, along with several questionable positives. Plaques were picked and plated for secondary screening. Reprobing showed a few faint plaques. Phagemids were induced and digestions were conducted on the DNAs. A Southern hybridization was performed on the digests and the two putative positives showed some homology to the putative nucA sequence (from pPX643; see below). When subjected to PCR amplification with 4101ext (SEQ ID NO:5) and 4102ext (SEQ ID NO:6) primers, the two positives did not show an amplification of the expected 420 bp band. The clones seemed to have limited homology to nucA and showed a different restriction pattern when compared to the PCR clone, pPX643.

Figure 5:
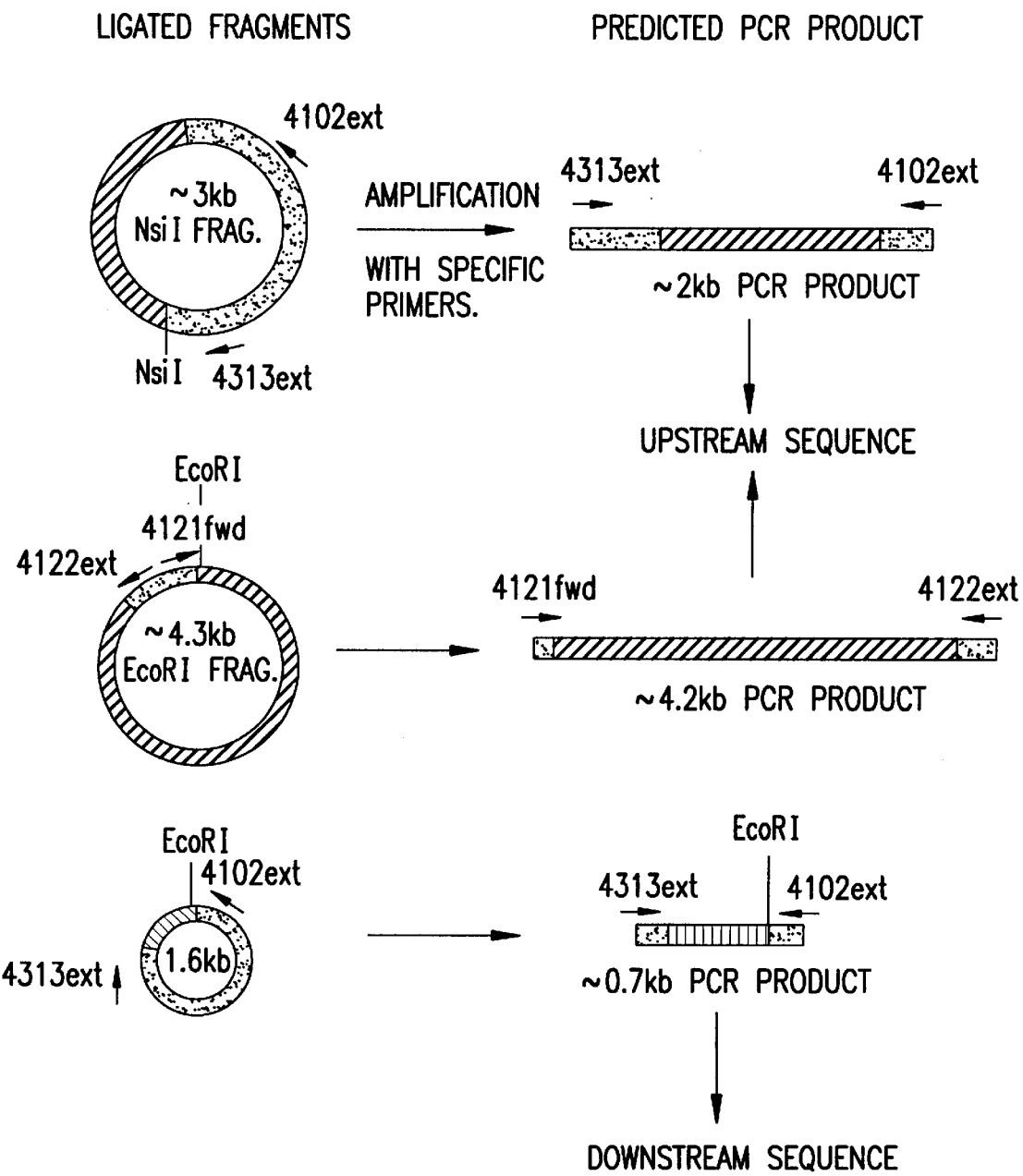
FIG. 5 depicts a schematic of predicted nucA-specific inverse PCR reactions and products. P860295 genomic DNA was digested with either NsiI (Top) or EcoRI (Middle & Bottom). The DNAs were diluted and ligated forming "self-ligated" circles. The DNA circles containing nucA DNA are shown.

3'-end nucA DNA—In order to obtain the DNA sequence of both the 5' and 3'-ends of the nucA gene (which are not present in the initial pPX640 construct), inverse PCR methodology was used as shown schematically in FIG. 5. Southern analysis of NTHi genomic DNA, digested with EcoRI or EcoRV and hybridized with the nucA-specific 420 bp DNA probe, yielded the following results: For EcoRI digested genomic DNA, two bands were detected at approximately 4.5 kb and 1.6 kb; for EcoRV digested DNA, one band was detected at approximately 7 kb. Ten-fold dilutions of these EcoRI and EcoRV digested P860295 genomic DNAs were then self-ligated using T4 DNA ligase (NEB). These DNAs were amplified using inverse PCR methodology with Taq DNA polymerase. Amplification cycles were as follows: 95° C. for 50 seconds, 52° C. for 90 seconds, 72° C. for 4 minutes, 30 cycles, and then 72° C. for 10 minutes. An aliquot of the reaction was electrophoresed in an agarose gel. With the EcoRI ligated DNA, primers 4121fwd (SEQ ID NO:17) GCTTTCAGCTAATGTGATTCC and 4122ext (SEQ ID NO:18) CATCACAGCTGCATCTGCAG were used for the upstream nucA DNA amplification reaction, and primers 4313ext (SEQ ID NO:7) and 4102ext (SEQ ID NO:6) were used for the downstream nucA DNA amplification reaction. The primer 4121fwd corresponds to nucleotides 669–689 of SEQ ID NO:1. The primer 4122ext corresponds to the complement of nucleotides 551–570 of SEQ ID NO:1 in the reverse direction. Primers 4122ext and 4313ext were used with the EcoRV ligated DNA for both upstream and downstream nucA DNA amplification. An approximately 1.3 kb fragment was observed for the nucA EcoRI downstream region. A faint approximately 2 kb fragment was observed for the EcoRV digested DNA. No DNA PCR product was observed for the nucA EcoRI upstream region. Other attempts to amplify the 5'-end of the nucA gene from either genomic DNA or from the NTHi λ Zap™II library DNA failed to produce either any DNA product or DNA sequence that matched nucA sequence obtained by other means. The approximately 1.3 kb PCR downstream product was directly sequenced as well as cloned into pCR™II vector and the plasmid named pPX800. From the DNA sequence data, the complete 3'-end sequence, the TAA stop codon and additional downstream noncoding sequence of the nucA gene were obtained. Genomic "mature" nucA cloning—In order to confirm and obtain the complete sequence of the mature nucA gene, a PCR reaction was done using the P1 degenerate (SEQ ID NO:3) and 63K Reverse (Rev) (SEQ ID NO:9) primers on nondigested P860295 genomic DNA. The 63K Rev primer has the following sequence, which is the complement of nucleotides 2095–2114 of SEQ ID NO:1 in the reverse direction:

63K Rev    GAAGTCTTCAAACCTAGGAC    (SEQ ID NO:9)

Approximately 1 μg of P860295 genomic DNA was used in a PCR reaction consisting of Taq DNA polymerase and these two primers. An aliquot of the reaction was electrophoresed in an agarose gel. The predicted size DNA fragment of approximately 1.8 kb was observed. This DNA fragment was gel purified and cloned into pCR™II and the plasmid named pPX643. The DNA sequence of nucA in pPX643 was determined and matched the sequence from earlier partial data sets. This clone contains the complete mature nucA sequence, but is missing the upstream promoter region and signal sequence.

5' Upstream sequence of nucA using PCR Several attempts were made to amplify the promoter region from DNA made from the P860295 λ library using the T3 and T7 primers coupled to several different nucA primers that had been synthesized during the sequencing of P1/T7 and P2/T3 clones. None of these reactions generated the required fragment. Attempts to amplify this region by inverse PCR from the EcoRI 4.3 kb fragment were also unsuccessful (see above). Other restriction fragments, preferably smaller than the 4.3 kb fragment, were therefore considered for inverse PCR. Southerns were performed on P860295 genomic DNA using the dig-dUTP labelled 420 bp chromosomal probe and restriction enzymes PstI, SalI, EcoRV, BamHI, ApaI, AvaI, KpnI, SacI, SmaI, XbaI, XhoI, and AT-rich enzymes, BglII, HindIII, NsiI, SnaBI, SspI and PacI. From these hybridizations, a limited genomic restriction map was obtained (see FIG. 4).

The NsiI digest gave an approximately 3 kb band that hybridized to the nucA 420 bp probe; this is one of the smaller pieces identified. Therefore, this 3 kb fragment was gel isolated from the genomic digest, self-ligated and set up for inverse PCR. An approximately 2 kb fragment was obtained in the amplification of the self-ligated NsiI fragment with the 4102ext (SEQ ID NO:6) and 4313ext (SEQ ID NO:7) primers. The primer 4313ext (SEQ ID NO:7) has the following sequence, which corresponds to nucleotides 1762–1779 of SEQ ID NO:1:

4314ext    GTGAGTGTTGAAGTCTTG    (SEQ ID NO:7)

The fragment was sequenced and cloned into the pCR™II vector. Eleven out of twelve colonies had inserts; ten were in one orientation (and named pPX679) and one was in the opposite orientation (and named pPX680). DNA sequencing of the insert within pPX680 produced about 1,020 bases of additional sequence upstream of the mature nucA gene. Hence, the clone contains the promoter region and signal sequence of the nucA gene. The sequence in the overlapping region matched with the sequence from previous clones (pPX640, the P2/T3 clone and pPX643, described above), confirming the clone to be nucA. See also SEQ ID NO:1.

Cosmid Library Construction A cosmid library was also constructed as follows: Genomic DNA from P810384 and P860295 was partially digested with Sau3AI to generate 30–50 kb fragments which were ligated into the BamHI site of SuperCosI vector, a plasmid constructed from λ DNA containing two integration sites (Stratagene). The host strain used was NM554 (Stratagene). Colonies were screened with an anti-NucA monoclonal antibody (Mab Nt63/2-13-42), polyclonal antibody and dig-labelled DNA probes.

Immunoblot Screening Of Cosmid Library Mab Nt63/2-13-42 did not react well to the P810384 strain on colony blots. Therefore, screening was stopped on the P810384 library. Several putative positives were identified from the P860295 library. The putative positives were streaked out and rescreened but they were of medium intensity. A Western was run on these positives (overnight cultures) and probed with Mab Nt63-34-25 which reacts strongly to denatured NucA. However, no NucA bands were seen on the Westerns. Therefore, as with the λ Zap™II library, immunoblot screening of the cosmid library was discontinued.

Colony hybridization on the cosmid library Similarly, the P860295 cosmid library was screened using the 420 bp dig-labelled probe. This screen produced 26 putative positives which were identified from five library filters. They were rescreened and only four were positive, of which two were strongly positive. Four isolated colonies were picked from one of the strong positives and DNA preps were made for Southern analysis. DNA from two colonies gave similar hybridization restriction patterns with EcoRI, HindIII, and ScaI&EspI digests, while the other two colonies gave different sized DNAs, one with a larger total insert size and one smaller. When the filter was washed at 70° C., the two similar colonies gave only background binding. The other two clones showed positive hybridization at 70° C. and were analyzed further by PCR. Only one, the larger sized clone, contained most of the 5' end of the nucA gene. Upon sequencing this cosmid clone, the nucA insert was found to start at a Sau3AI site, 55 bases in from the start of the mature sequence, and proceeded downstream from that site; therefore, it was missing the signal sequence and an additional 55 bases from the 5' end of the mature gene.

PCR on cosmid library Similarly, the packaged phage from the cosmid library was amplified using 63K P1 Rev (SEQ ID NO:19) CTTAATTCCACAGCTTTGTGAGC (where the 18th base may also be A and the 21st base may also be T) and T3 (SEQ ID NO:7) or T7 (SEQ ID NO:8) primers to pull out the upstream sequence. The primer P1 Rev corresponds to the complement of nucleotides 319–341 of SEQ ID NO:1 in the reverse direction. Reactions were also conducted with the 4122ext (SEQ ID NO:18) primer and the T3 or T7 primers. At 42° C., three smeary bands were seen at approximately 250, 400 and 550 bp, with the nucA P1 Rev/T3 or T7 pairs, all of which hybridized to the 420 bp probe. No bands were obtained with the 4122ext/T3 primer pair. Similar smeary bands were seen with the 4122ext/T7 primers. At 50° C., only the 250 bp band was obtained in all four reactions. T3 or T7 alone gave no bands, and the T3/T7 primer pair gave very smeary approximately 550 and 300 bp bands. The three smeary PCR products from the nucA P1 Rev/T7 and 4122ext/T7 PCR reactions were purified through a QIAquick™ column (Qiagen, Chatsworth, Calif.), eluted with 50 µl water, and 2 µl of it was cloned into the pCR™II vector. Four of the six clones had inserts, with three different inserts obtained for the nucA P1 Rev/T7 PCR product. However, only the approximately 350 bp insert was obtained with the 4122ext/T7 PCR product (seven of eight had the insert). The sequence for the 4122ext/T7 clone corresponded to the nucA sequence starting at the Sau3AI site, 55 bases in from the 5' end of the mature sequence, which was similar to the cosmid clone described above.

Assembly of the Complete nucA Sequence The complete nucA sequence was assembled from the overlapping clones containing 5' upstream sequence, 3' downstream sequence and the partial mature sequence described above. The complete nucA gene sequence is set forth in SEQ ID NO:1, nucleotides 229–2037. The signal peptide is encoded by nucleotides 229–303. The mature NucA protein is encoded by nucleotides 304–2037.

Example 3

Expression Of NucA Protein

The nucA gene was then cloned and expressed in *E. coli*, either as a fusion protein or as a full-length NucA protein (with a signal peptide). The nucA gene was ligated into various *E. coli* expression vectors as listed in Table 1 and the cultures were appropriately induced for expression of the NucA protein. Whole cell lysates were normalized and run on a SDS-PAGE gel, and either stained with Coomassie or transferred to a nitrocellulose membrane and probed with rabbit anti-NucA polyclonal antibodies at a 1:500 dilution in 5% BLOTTO. The clones are listed in Table 1 and were constructed as described below.

A fusion protein containing the NucA protein plus heterologous residues was expressed by cloning the nucA gene from plasmid pPX643 into the pRSET expression vector (see FIG. 6). Plasmid pPX643 contains the complete mature nucA sequence cloned into pCR™II vector, as described in Example 2. The version of pRSET chosen was that having the reading frame designated "C" by the manufacturer. The vector contains the gene 10 T7 promoter, the ampicillin resistance gene and has the ColE1 DNA origin of replication.

pPX644 Construction—Plasmids pPX643 and pRSETC were digested with Asp718 restriction enzyme, purified by GENECLEAN method, redigested with XhoI enzyme, and the DNAs electrophoresed on an agarose gel. The approximately 1.9 kb nucA-containing DNA fragment was isolated and ligated to the pRSETC isolated DNA. The resulting clone was called pPX644. BL21(DE3)pLysS transformants were called RZ1034.

The recombinant clone, pPX644, contains 51 additional amino acids fused to the N-terminal region of the mature nucA protein. These additional amino acids are provided by the vector and include six histidines in series just downstream of the initial methionine, which aid in the purification of the fusion protein. Whole cell extracts from induced cultures containing this plasmid were electrophoresed on an SDS-PAGE and a Western blot performed using rabbit polyclonal antisera against the NucA protein. Overnight cultures of RZ1034 isolates and BL21(DE3)pLysS/pRSETC were inoculated into 10 ml modified SOB (20 g tryptone, 5 g yeast, 0.6 g NaCl, 0.2 g KCl, adjusted to pH 7.0 with 5N NaOH) plus ampicillin (100 µg/ml) in a 125 ml flask and grown at 37° C. to a Klett colorimeter reading of 126–155. One ml aliquot of uninduced cells was removed, centrifuged and resuspended with TE buffer (10 mM Tris-HCl, pH 8.0, 1 mM EDTA) to the same volume in microliters (µls) as the Klett reading, i.e., a Klett reading of 126 means cells were resuspended using 126 µl TE buffer. For induction, IPTG was added to the growing culture to a final concentration of 1 mM and the incubation continued for two hours with a final Klett reading determined. One milliliter was removed and centrifuged in a 1.5 ml Eppendorf tube. The cell pellet was resuspended in TE buffer, again based on its respective final Klett reading. Ninety µl each, of uninduced and induced cells, was removed to another Eppendorf tube, 30 µl of a 4× Cracking Buffer was added and the tube heated in a boiling water bath for 10 minutes prior to running 20 µl on a 4–15% gradient SDS-PAGE gel (Bio-Rad Laboratories). The protein bands were transferred to nitrocellulose filter paper and a Western blot performed using rabbit polyclonal NucA antisera and anti-rabbit Ig peroxidase (Tago Inc.). The bands were visualized using TMB reagent (Promega, Madison, Wis.). A predicted 69 kD size protein product was clearly detected in the blot as shown in FIG. 7. This confirmed the correct cloning of the nucA gene. In this example, the lack of observed inducibility of NucA was presumably due to the absence of the antibiotic, choloramphenicol, in the growth medium which is required for stable maintenance of the pLysS plasmid (which carries the chloramphenicol resistance gene). Hence, loss of the pLysS plasmid would result in a high basal (uninduced) level of expression of NucA. In a separate experiment, the 69 kD NucA protein was shown to be inducible in a Western blot when chloramphenicol was included in the growth medium (data not shown). Although the 69 kD protein band can be detected in a Western blot, it was not detected in a similar SDS-PAGE gel stained with Coomassie (data not shown). Without being bound by the following, one possible reason for not detecting the recombinant protein in the Coomassie gel may be due to the 51 additional, vector-encoded, amino acid residues at the N-terminal end of the cloned nucA gene in pPX644.

A mature clone that did show a level of expression visible in a Coomassie gel was constructed using a slightly different fusion approach. This clone, called pPX693, was constructed as follows:

pPX682 Construction—The nucA gene was PCR amplified from P860295 genomic DNA using RSET-5 primer (SEQ ID NO:15), which has the following sequence whose last 17 bases somewhat correspond to nucleotides 304–320 of SEQ ID NO:1 (the primer was based on the pPX643 sequence which was generated using the degenerate primer P1):

RSET-5 GCTACGGCTAGCAAAGAAGCACCTCAAGC (SEQ ID NO:15)

and the 63K RBam primer (SEQ ID NO:13). (RSET-5 was designed to include a BamHI site at the 5' end for facilitating the transfer of the nucA fragment to the pRSET expression vector; see below). The amplified DNA fragment was cloned into the pCR™II vector and was designated pPX682. This construct encodes mature length NucA.

pPX693 Construction—The nucA BamHI fragment from pPX682 was ligated into the BamHI site of the expression vector pRSETC and the resulting plasmid was called pPX693. This resulted in a clone which expressed a fusion NucA with an additional 38 amino acids at its N-terminus. Upon cleavage with enterokinase, all but five amino acids would be removed. The pRSETC vector also contains a polyhis region which allowed the purification of the fusion protein over a nickel column prior to cleavage by enterokinase. The clone pPX693 when transformed into the E. coli BL21(DE3)pLysS strain and induced with IPTG showed a significant level of expression that was detectable on Coomassie stained gels. FIG. 8 shows that it was the major protein band in the cell lysate. However, upon growing up a larger culture for protein purification, the expression was undetectable by Coomassie staining. It was found that the plasmid was not stably maintained in the expression strain. Subsequently, other clones were obtained with acceptable levels of expression, so further work to stabilize pPX693 was not undertaken.

Native signal sequence After the upstream sequence was obtained from the clone pPX680 (an approximately 2 kb NsiI inverse PCR product cloned into pCR™II vector, as mentioned in Example 2), primers NdeF63K and NcoF63K were used to amplify the full length native nucA gene from genomic P860295 DNA. The PCR product was cloned into two different expression vectors, pRSETC and pTrcHisC (FIG. 9). These vectors have been maximized for expression using strong promoters that are inducible by IPTG. Plasmids pPX685, pPX688, pPX691 and pPX692, referred to in Table 1, were constructed as follows:

pPX685 Construction—The full length nucA gene was cloned by PCR amplification from the genome of P860295. The primers used were NdeF63K and 63K RBam. Primer NdeF63K is SEQ ID NO:1, nucleotides 229–255 with an NdeI site attached at the 5' end for later transfer into pRSETC. The PCR product, cloned into pCR™II vector, is called pPX685.

pPX692 Construction—Subcloning of the complete nucA sequence from pPX685 into pRSETC produced pPX692. Specifically, pPX685 was digested with NdeI and BamHI, the full length nucA fragment was isolated and ligated into pRSETC which had also been digested with NdeI and BamHI. The resulting plasmid was called pPX692. When pPX692 was transformed into the E. coli BL21(DE3)pLysS strain and induced with 1 mM IPTG, a similar Coomassie level of NucA protein was obtained (see FIG. 10A) compared to pPX693 (see FIG. 8A).

pPX688 Construction—The full length nucA gene was cloned from genomic P860295 DNA using PCR and primers NcoF63K and 63K RBam. Primer NcoF63K is SEQ ID NO:1, nucleotides 229–255 with an NcoI site and a few extra bases for translational frame adjustment attached at the 5' end, specifically bases ACCATGGGT, for subsequent subcloning into pTrcHisC. The PCR product was cloned into the pCR™II vector and the resulting plasmid called pPX688. The NcoI linker added two amino acids to the N-terminal start region of the signal sequence.

pPX691 Construction—Subcloning of the complete nucA sequence from pPX688 into pTrcHisC (see FIG. 9) produced pPX691. Specifically, pPX688 was digested with NcoI and BamHI, the full length nucA fragment was isolated and then ligated into pTrcHisC which had also been digested with NcoI and BamHI. When pPX691 was transformed into the E. coli InvαF' strain and induced with 1 mM IPTG, a similar Coomassie level of NucA protein was obtained (see FIG. 10A) as compared to pPX693 (see FIG. 8A). The NcoI restriction site added two residues to the very beginning of the native signal sequence, which appeared not to affect the processing of the NucA signal sequence, as shown in FIGS. 10A and 10B. The apparent molecular weight of the expressed protein seemed to be about 63 kD for a processed protein, rather than 66 kD for an unprocessed protein. The band at about 63 kD seemed to be the major protein band in the Coomassie stained gel. Upon purification and amino acid sequence analysis, it was shown to be processed. See Example 4 on protein sequencing.

The plasmid pPX691 was grown up in a 2 L culture for purification together with pPX693 (fusion protein). However, it was found that pPX693 was not stably maintained in the BL21(DE3)pLysS host, while pPX691 was stably maintained in DH5α or InvαF' hosts. Plasmid pPX691 was chosen to be the clone of choice for protein purification of rNucA. A stability study on pPX692 was not done, since its expression was not any better than pPX691. See FIGS. 10A and 10B.

TABLE 1

E. coli Vectors Expressing The NucA Protein

| nucA sequence | Vector | Site(s) of insert | Parent Plasmid | Promoter | pPX# | Additional Fusion aa | Expression |
|---|---|---|---|---|---|---|---|
| mature | pRSETC | XhoI, Asp718 | pPX643 | T7 | pPX644#7 | 51 (20 after EK) | +W |
| mature | pRSETC | BamHI | pPX682 | T7 | pPX693* | 38 (5 after EK) | +W, +C |
| mature | pRSETC/TIR | BamHI | pPX693 | T7 | pPX709 | 41 (5 after EK) | −C |

TABLE 1-continued

E. coli Vectors Expressing The NucA Protein

| nucA sequence | Vector | Site(s) of insert | Parent Plasmid | Promoter | pPX# | Additional Fusion aa | Expression |
|---|---|---|---|---|---|---|---|
| full | pRSETC | NdeI, BamHI | pPX685 | T7 | pPX692 | 0 | +W, +C |
| full | pTrcHisC | NcoI, BamHI | pPX688 | trc | pPX691 | 2 (before signal) | +W, +C |
| OmpT | pET12a | BamHI | pPX706 | T7 | pPX707 | 4 (after signal) | +W, +C |
| PelB | pET20b | BamHI, EcORV | pPX705 | T7 | pPX708 | 3 (after signal) | +W, +C |

W = By Western Analysis
C = By Coomassie gel analysis
*plasmid is not stably maintained
EK = enterokinase cleavage Although the Haemophilus-encoded nucA signal sequence seemed to allow good expression of rNucA in E. coli, as well as being processed correctly (i.e. removal of the signal sequence), two commercially available E. coli expression vectors, containing different signal sequences, were tried. PelB (pPX708 [made from pPX705] in pET20b vector, Novagen) and OmpT (pPX707 [made from pPX706] in pET12a vector, Novagen) were separately cloned upstream of the mature nucA gene as follows:

PelB Construction—The nucA gene was PCR amplified from pPX643 using primers 63K PelB (SEQ ID NO:12), which has the following sequence whose last 17 bases somewhat correspond to nucleotides 304–320 of SEQ ID NO:1 (the primer was based on the pPX643 sequence which was generated using the degenerate primer P1):

63K PelB  GATATCAAAGAAGCTCCTCAAGC    (SEQ ID NO:12)

and 63K RBam (SEQ ID NO:13), which has the following sequence, whose last 21 bases are the complement of nucleotides 2095–2115 of SEQ ID NO:1 in the reverse direction:

63K RBam  CGCGGATCCTGAAGTCTTCAAACCTAGGAC  (SEQ ID NO:13)

The approximately 1.8 kb nucA-containing PCR DNA band was gel isolated, cloned into pCR™II and the resulting plasmid called pPX705.

pPX708 Construction—Both plasmids pPX705 and pET20b were digested with EcoRV and BamHI, DNAs electrophoresed on an agarose gel and the correct DNA bands isolated. The DNAs were ligated together and the resulting plasmid called pPX708. BL21(DE3)pLysS transformants were called RZ1070.

OmpT Construction—The nucA gene was PCR amplified from pPX643 using primers 63K OmpT (SEQ ID NO:14), which has the following sequence whose last 17 bases somewhat correspond to nucleotides 304–320 of SEQ ID NO:1 (the primer was based on the pPX643 sequence which was generated using the degenerate primer P1):

63K OmpT  GGATCCAAAGAAGCTCCTCAAGC    (SEQ ID NO:14)

and 63K RBam (SEQ ID NO:13). The approximately 1.8 kb nucA-containing PCR DNA band was gel isolated, cloned into pCRTmII and the resulting plasmid called pPX706.
pPX707 Construction—pET12a vector DNA was digested with BamHI enzyme, treated with calf intestine alkaline phosphatase (Boehringer Mannheim), electrophoresed on an agarose gel, and the DNA isolated. The plasmid pPX706 was digested with BamI enzyme, electrophoresed on an agarose gel, and the approximately 1.8 kb nucA-containing DNA fragment gel isolated. Both the pET12a and pPX706 gel isolated DNAs were ligated together and the resulting plasmid called pPX707. BL21(DE3)pLysS transformants were called RZ1065.

PelB-NucA & OmpT-NucA Expression One ml of overnight cultures of RZ1065 (pPX707: OmpT-nucA clone) and RZ1070 (pPX708: PelB-nucA clone) were each inoculated into 20 mls SOB plus chloramphenicol (30 µg/ml) plus ampicillin (100 µg/ml) in a 125 ml flask and grown at 37° C. to O.D.$_{600}$=1.0–1.3. Ten mls of the culture were transferred to another 125 ml flask and IPTG added to a final concentration of 1 mM. Both uninduced and induced cultures were grown at 37° C. for an additional two hours. One ml of each of the cultures was removed and centrifuged in a 1.5 ml Eppendorf tube to pellet the cells. The supernatants from the induced cultures were saved. The cell pellets were resuspended with 0.6–1.6 ml PBS to O.D.$_{600}$ of approximately 1.0. One ml of the resuspended cells was recentrifuged and resuspended with 60 µl H$_2$O. To 60 µl of the resuspended cells or 60 µl of the supernatant was added 20 µl of a 4× Cracking Buffer and the tube heated in a boiling water bath for five minutes. Twenty µl of each sample was electrophoresed on a 12% SDS-PAGE gel and stained with Coomassie blue. Both the OmpT and PelB NucA-fusion proteins were detected and were of the correct size for a processed protein (FIG. 11). The yield of the PelB NucA-fusion protein expression was approximately 30% of the total cellular protein, which was comparable to the expression of full length NucA (with native signal, pPX691; see FIG. 12 below).

FIG. 12 shows a comparison of expression from several signal sequence clones and also from a mature fusion clone with an optimized translation initiation region (TIR) sequence (11), pPX709. The clone pPX709 was constructed from clone pPX677 as follows:

pPX677 Construction—Plasmid pRSETC was digested with NheI enzyme, phenol extracted, ethanol precipitated and redigested with NdeI enzyme. The DNA was electrophoresed on an agarose gel and the DNA band gel isolated. An Nhe1+Nde1 linker was constructed by annealing the RSET.TIR top oligo (SEQ ID NO:10), which has the following sequence (which does not correspond to nucA):

```
RSET.TIR top    TATGGCTATGTCTAACATGACTTACAAACATCATCATCAT   (SEQ ID NO:10)
                CATCATGGTATGG
``` to the RSET.TIR bottom oligo (SEQ ID NO:11), which has the following sequence (which does not correspond to nucA):

```
RSET.TIR bottom    CTAGCCATACCATGATGATGATGATGTTTGTA   (SEQ ID NO:11)
                   AGTCATGTTAGACATAGCCA
```

This linker was ligated to the NheI+NdeI digested PRSETC purified DNA and the resulting plasmid called pPX677.

pPX709 Construction—Plasmid pPX677 was digested with BamHI, treated with calf intestine alkaline phosphatase (Boehringer Mannheim), electrophoresed on an agarose gel, and the DNA isolated. Plasmid pPX693 was digested with BamHI, electrophoresed on an agarose gel, and the DNA isolated. The isolated DNAs were ligated together and the resulting plasmid called pPX709. BL21(DE3)pLysS transformants were called RZ1076.

The pPX691 (native signal sequence) clone and vector-alone control were induced at O.D.$_{600}$ of 0.8–0.9 with 1 mM IPTG for one hour. The pPX707 (OmpT signal), pPX708 (PelB signal) and pPX709 (TIR) clones were induced at an O.D. of about 1.0 for two hours. All cultures were normalized to an O.D. of about 1.0 and equal volumes were loaded onto the gel. P860295 was grown for about 3.5 hours to an O.D. of about 1.6, then normalized to about 1.0. Induced pPX691 and induced pPX708 definitely showed an intense NucA band; in fact, it appeared to be the major protein band. However, pPX707 and pPX709 did not produce an obvious NucA induced band. This shows that not all signal sequences or "optimized" expression vectors produce a high level of induced NucA protein.

Example 4

NucA Protein Purification And Characterization

Purification Of nNucA Protein From NTHi

Whole cell extract preparation Whole bacterial cells (about 70 g wet weight of NTHi) were suspended in 200 ml of 0.1M potassium phosphate (KPO$_4$)/3.0M KSCN (pH 6.0) and stirred at room temperature for 60 minutes to extract nNucA protein. Cell debris was removed by centrifugation at 8,000 rpm using a Sorvall GS-3 rotor for 20 minutes at 4° C. The supernatant was collected and further clarified by centrifugation at 60,000 rpm using a Beckman 70Ti rotor for 60 minutes at 4° C. The supernatant was collected and dialyzed overnight at 4° C. against 50 mM NaPO$_4$ (pH 8.0).

Column chromatography The dialyzed whole cell extract was loaded onto a 25 mL Ceramic Hydroxyapatite (HA) column (80 μm Bio-Rad) equilibrated in 50 mM NaPO$_4$ (pH 8.0). Bound protein was eluted with a 0.2M NaPO$_4$ step, followed by a linear NaPO$_4$ gradient (0.2–0.5M NaPO$_4$). Fractions were screened for nNucA via SDS-PAGE and Western analysis and positive fractions pooled. The HA step was performed three times with three independent whole cell extract preparations. Native NucA from each of the three HA runs was pooled together and concentrated about 7-fold using an Amicon stirred cell with a PM10 membrane. The HA concentrate was dialyzed overnight at 4° C. against two 2 L changes of 50 mM Tris-HCl/1 mM EDTA (pH 9.0). The material was loaded onto a MonoQ HR5/5 column (Pharmacia) equilibrated in 50 mM Tris-HCl/1 mM EDTA (pH 9.0). Bound protein was eluted with a linear NaCl gradient (0–1.0M NaCl in 50 mM Tris-HCl/1 mM EDTA (pH 9.0)). Fractions were screened for nNucA via SDS-PAGE and pooled. A total of 2.5 mg of purified nNucA was isolated from about 70 g wet weight of NTHi cells. Native NucA protein purified using this protocol exhibits a single band on a SDS-PAGE gel corresponding to a molecular mass of about 63,000 Daltons.

NaCl Extraction Of nNucA The following extraction protocol for nNucA protein was used as an alternative to extraction by KSCN. Bacterial cells (about 37.5 g wet weight of NTHi) were suspended in 150 ml 50 mM NaPO$_4$ (pH 7.0) and disrupted by three passages through a French pressure cell at 1000 psi. Cell debris and membranes were pelleted by centrifugation at 55,000 rpm using a Beckman 70Ti rotor for 20 minutes at 4° C. The pellet was resuspended in 132 ml 10 mM HEPES/1.0M NaCl (pH 7.5) and stirred at 4° C. for 20 minutes to extract the nNucA protein. Cell debris and membranes were removed by centrifugation at 60,000 rpm using a Beckman 70Ti rotor for 60 minutes at 4° C. The supernatant was collected and dialyzed overnight at 4° C. against 50 mM NaPO$_4$ (pH 8.0). Subsequent HA and MonoQ Chromatography steps were performed as described above for the native NucA protein. Yields of nNucA using NaCl extraction were comparable to those obtained with the other method described above.

Purification Of rNucA Protein

Crude extract preparation A process utilizing cell lysis via passage through a French pressure cell and two chromatographic steps was developed for the purification of rNucA protein. Bacterial cells expressing rNucA (about 30 g wet weight of E. coli InvαF'/pPX691) were suspended in 80 ml 50 mM Tris-HCl/1 mM EDTA (pH 8.0) and disrupted by three passages through a French pressure cell at 1000 psi. Cell debris and membranes were removed by centrifugation at 55,000 rpm using a Beckman 70Ti rotor for 20 minutes at 4° C. The supernatant was collected and dialyzed overnight at 4° C. against two 4 L changes of 50 mM Tris-HCl/1 mM EDTA (pH 8.0).

Column chromatography The dialyzed crude extract supernatant was loaded onto a 50 ml trimethylaminoethyl (TMAE) Fractogel™ anion exchange column (EM Separations Technology) equilibrated in 50 mM Tris-HCl/1 mM EDTA (pH 8.0) at room temperature. Most of the contaminating proteins bound to the column. The column flow through, containing rNucA protein as well as several contaminant proteins, was collected and dialyzed overnight at 4° C. against 20 mM HEPES/1 mM EDTA (pH 7.0). The material was then loaded onto a MonoS HR10/10 cation exchange column (Pharmacia) equilibrated in 20 mM HEPES/1 mM EDTA (pH 7.0) which binds the NucA protein. Bound protein was eluted with a linear NaCl gradient (0–1.0M NaCl in 20 mM HEPES/1 mM EDTA (pH 7.0)). Most of the rNucA eluted at about 0.4M NaCl. Fractions were screened for rNucA via SDS-PAGE and pooled. A total of 80 mg of purified rNucA was isolated from about 30 g wet weight of cells. The rNucA protein purified using this protocol exhibited a single band on a SDS-PAGE gel corresponding to a molecular mass of about 63,000 Daltons.

Amino Acid Sequence Analysis

For amino acid sequence analysis of the native protein, about 250 μl of the sample containing 100 μg of purified protein was precipitated with 90% ethanol for 30 minutes at 0° C., followed by centrifugation in a microcentrifuge. The pellet was resuspended in 20% acetic acid and subjected to amino terminal amino acid sequence analysis. For the recombinant protein, 80 μl of the sample containing 80 μg of rNucA was added to a ProSpin cartridge (Applied Biosystems, Foster City, Calif.) and centrifuged. The polyvinylidene difluoride (PVDF) membrane containing the sample was removed and washed with 20% methanol. The membrane was subjected to amino terminal amino acid sequence analysis.

Amino terminal amino acid sequence analysis was carried out using an Applied Biosystems Model 477A Protein/Peptide Sequencer equipped with an on-line Model 120A PTH Analyzer (Applied Biosystems). After the cleavage of each successive amino-terminus, the anilinothiazolinone derivative formed was converted to the more stable phenylthiohydantion (PTH) derivative by treatment with 25% trifluoroacetic acid (TFA) at 64° C. for 20 minutes. The PTH derivatives were separated and identified on the PTH analyzer by reversed-phase HPLC using a Brownlee PTH C-18 column (particle size 5 mm, 2.1 mm internal diameter×22 cm length; Applied Biosystems) with a two solvent gradient system according to manufacturer's instructions.

For the native protein, the first 26 residues (SEQ ID NO:2, residues 26–51) were unambiguously identified except for an additional unidentified peak at residue 1. For the recombinant protein, 18 of the first 19 residues (SEQ ID NO:2, residues 26–44) were unambiguously identified. Both residues 1 and 2 contained an additional unidentified peak and residue 13 (SEQ ID NO:2, residue 38) could not be identified. Concurrence of the amino terminal sequence of the recombinant NucA protein with that of the native protein indicated identical post-translational processing of the signal sequence in the protein expressed in E. coli to that in Haemophilus.

Example 5

Nucleotidase Activity Of NucA Protein

Ectoenzymes are defined as intrinsic membrane proteins with their catalytic sites on the extracellular surface of the membrane (12). One class of ectoenzyme is the ectophosphohydrolase (5'-nucleotidase). There are many reports dealing with both bacterial and mammalian 5'-nucleotidases, each showing different substrate reactivities. Mammalian 5'-nucleotidase enzyme uses AMP (adenosine monophosphate nucleotide) as a substrate producing A (adenosine nucleoside) and P (phosphate) whereas bacterial enzymes may use ATP (adenosine triphosphate nucleotide), ADP (adenosine diphosphate nucleotide) and AMP, as well as other nucleotides.

One of the early reports studying the E. coli 5'-nucleotidase protein suggested that it was located in the periplasmic space of the cellular membrane and that this protein was unique because it had both sugar hydrolase and mononucleotidase activity (13; 14). A later study by Burns and Beacham (15) presented a nucleotide sequence analysis and N-terminal protein sequence of the mature E. coli 5'-nucleotidase gene, ushA. Based on the protein sequence and the DNA gene sequence, the UshA protein contains a signal sequence which is proteolytically removed in the mature protein. The predicted mature protein molecular weight is 58 kD.

Marine luminous Vibrio and Photobacterium strains contain a membrane bound specific 5'-nucleotidase enzyme (16). The holophilic marine bacterium Vibrio parahaemolyticus encodes a 5'-nucleotidase gene called nutA (17). The nutA gene has been cloned, sequenced and expressed in E. coli. The 5'-nucleotidase enzyme may be a lipoprotein inserted into the outer membrane. 5'-nucleotidase activity has also been detected in gram positive bacterium Bacillus subtilis (18).

Amino Acid Comparison

An amino acid comparison of rat liver 5'-nucleotidase, E. coli 5'-nucleotidase (UshA) and 2',3'-cyclic phosphodiesterase showed one region of striking homology, suggesting that this domain may be involved in the catalytic activity and/or binding of substrate (19). A further comparison of various 5'-nucleotidase sequences, rat, human, UshA, NutA and NucA, revealed two very strong homologous regions. These regions span amino acids 119–152 of the NucA sequence from SEQ ID NO:2. For example, complete homology of the NucA amino acid sequence with the human nucleotidase amino acid sequence is present at residues 124–130 and 148–151 of SEQ ID NO:2. Although the overall degree of homology between NucA and human nucleotidase proteins is very small and limited mainly to these regions described above with four or more consecutive homologous amino acids, deletion of either or both of these regions should reduce any potential immune cross-reactivity of a vaccine containing the NucA protein.

5'-Nucleoside Release Assay

A protein search was done via the NCBI BLAST E-mail service using the nucA gene sequence. The search suggested some limited amino acid homology with known 5'-nucleotidase precursors across species, i.e., human, rat and E. coli. A Lipman-Pearson protein alignment (DNAStar) was performed comparing NucA protein with rat nucleotidase protein. A 33.0 Similarity Index was determined comparing NucA (amino acids 36–333) to rat nucleotidase (amino acids 30–329). An initial 5'-nucleoside release assay was performed using rat 5'-nucleotidase reaction conditions as described by Ikehara et al. (20) to determine whether the NucA protein possesses 5'-nucleotidase activity.

A 5'-nucleotide such as AMP is a polar substrate which will not migrate on a TLC plate when a solvent such as methanol/chloroform is added. A nucleotidase will cleave off the phosphate group, leaving the adenosine which is less polar. Adenosine will migrate on the plate in the presence of methanol/chloroform. Thus, a TLC spot which has migrated signifies that the AMP has been cleaved by a nucleotidase.

One-tenth of an ml of NTHi P860295 cells was centrifuged, washed with PBS buffer, and resuspended with 10 μl PBS. Purified rNucA and nNucA protein concentrations were at 200 μg/ml. 5'-nucleotidase reactions (100 μl) were performed in 1.5 ml Eppendorf tubes, each containing 0.1M Tris-HCl, pH 7.5, SmM MgCl$_2$, 0.1M KCl, 5 mM AMP, with or without added cells or protein. Each tube was incubated at 37° C. for 60 minutes. Two μl of the reaction was spotted on a silica TLC fluorescent plate and eluted with 20% methanol in chloroform. The plate was then viewed using a short wave, 254 nm, UV source. As shown in FIG. 13, both the recombinant and native purified NucA protein, as well as P860295 cells, exhibited 5'-nucleotidase activity. Phosphate Release Assay In a more quantitative 5-nucleotidase assay, inorganic phosphate released upon hydrolysis of 5'-nucleotides was determined calorimetrically using a modification of the method of Chen et al. (21). Reaction mixtures contained 100 mM Tris-HCl (pH 9.0), 6.6 mM $MgCl_{21}$ 1.65 mM 5'-AMP (or other nucleotide substrate) and enzyme in a final volume of 750 µl. The reaction mixture was incubated at 37° C. for 30 minutes and the reaction stopped with the addition of 250 µl of 20% TCA. Controls were run for each reaction in which enzyme was added after the addition of 20% TCA. Precipitated protein was removed via centrifugation and 200 µl of supernatant was withdrawn into a fresh test tube. One hundred microliters of 1.0N HCl was added, followed by the addition of 750 µl of ammonium molybdate reagent (3.0 ml 10% ascorbic acid plus 18 ml 3.4 mM ammonium molybdate in 1N $H_2SO_4$) and the mixture incubated at 37° C. for 30 minutes. After allowing the tubes to cool to room temperature, the absorbance at 650 nm was determined. One unit of 5'-nucleotidase activity is defined as the amount of enzyme which results in an absorbance change of 1.0 at 650 nm $min^{-1}$ at 37° C.

pH Optimum The optimum pH for the hydrolysis of 5'-AMP was found to be between 8.5 and 9.0 (data not shown); however, pH's above 9.0 were not examined. Effect of $Mg^{++}$ Divalent cations, in particular $Mg^{++}$, have been shown to stimulate or in some cases be an absolute requirement for 5'-Nucleotidase activity in both procaryotic and eucaryotic systems (16). The rNucA protein was also shown to be stimulated by the addition of $MgCl_2$. The addition of up to 6.6 mM $MgCl_2$ results in an approximately 2-fold stimulation of enzymatic activity (data not shown).

Substrate specificity The rNucA 5'-nucleotidase was shown to exhibit a relatively broad substrate specificity profile. The enzyme was shown to hydrolyze a variety of 5'-mono, di, and tri-phosphate nucleotides in addition to 5'-AMP. For all the nucleotides examined, the mono-phosphate nucleotide appeared to be the preferred substrate, except in the case of uridine, where UTP was preferred over UMP or UDP. The rNucA 5'-nucleotidase appeared to be specific for 5'-nucleotides as it displayed no activity with 3'-AMP (data not shown).

Phosphatase Assay

A phosphatase assay was conducted to determine whether the NucA protein possesses non-specific hydrolyzing activity in addition to its specific 5'-nucleotidase activity. Phosphatase was assayed using p-nitrophenylphosphate (PNPP) as substrate. Reaction mixtures (final volume 750 µl) contained 100 mM Tris-HCl (pH 9.0), 25 mM PNPP, and rNucA. The reaction mixture was incubated at 37° C. for 30 minutes and the reaction stopped by placing the tubes on ice. The absorbance at 410 nm was determined. Recombinant NucA had no detectable activity with PNPP (data not shown). This suggests NucA is a nucleotidase without phosphatase activity. In contrast, E. coli UshA has phosphatase activity in addition to its known nucleotidase activity (13; 14).

Example 6

Monoclonal Antibody Inhibition Of rNucA 5'-Nucleotidase

Monoclonal antibody (MAb) Nt63-34-25, raised to purified nNucA protein as described in Example 7 below, was tested for its ability to inhibit and/or precipitate the enzymatic activity of rNucA. MAb Nt63-34-25 has been shown to cross-react with rNucA as well as nNucA (data not shown). Inhibition or precipitation of enzyme activity by the anti-nNucA MAb would confirm that the rNucA protein is indeed a 5'-nucleotidase. Increasing concentrations of Mab (0, 2.5, 5, 10, and 20 µl) were incubated overnight at 4° C. with purified rNucA protein. An identical series was set up which also contained 50 µl of Protein A beads (Pierce) in addition to rNucA protein and MAb in order to facilitate immunoprecipitation. The mixtures were centrifuged and the supernatants subsequently assayed for 5'-nucleotidase activity using the phosphate release assay as described above. Percent activity, relative to the control containing no MAb, was calculated. FIG. 14 shows that the 5'-nucleotidase activity was inhibited as the concentration of MAb Nt63-34-25 was increased. The addition of 10 µl of MAb resulted in about 25% inhibition of enzyme activity while the addition of 20 µl exhibited about 45% inhibition. The effect of the MAb is enhanced if Protein A beads are added to facilitate immunoprecipitation of the rNucA protein. In the presence of Protein A beads, the addition of 10 µl of MAb resulted in an about 60% drop in 5'-nucleotidase activity while the addition of 20 µl exhibited about 80% inhibition. Complete inhibition of 5'-Nucleotidase activity was achieved with higher concentrations of MAb Nt63-34-25 (data not shown). These data confirm that the rNucA protein is indeed a 5'-nucleotidase.

Example 7

Generation of Antibodies And Animal Studies

Production of Hybridomas for monoclonal antibodies

Purified NucA protein preparations as described above were used in immunizing mice for generation of monoclonal antibodies. Female, eight week old BALB/c mice were inoculated intraperitoneally three times in a four week period (week 0, 2, 4) with 5 µg of NucA protein purified from NTHi strain P860295 and 25 µg of MPL™ adjuvant in 0.1 ml dose. Two separate fusion procedures were performed. The first fusion took place after a three month rest period using an intraperitoneal (IP) boost dose of 0.5 µg NucA protein; the second fusion took place after a four month rest period using an IP boost dose of 5 µg NucA protein by same route. During immunization and the rest period, mouse sera were obtained (week 0, 6) and tested for antibody activity by ELISA by using NucA protein as the coating antigen.

For both fusions, spleens were recovered from two immunized mice about 72 hours after the last injection, and were combined with nonsecreting X63Ag8.653 mouse (BALB/c) myeloma cells in 7:1 or 5:1 ratios (splenocytes:myeloma), respectively, for first and second fusion. The cells were fused for four minutes in 50% (wt/wt) polyethylene glycol 1500 and 10% dimethyl sulfoxide in Dulbecco's Modified Eagle medium (D-MEM). The fused cells were diluted in selection medium, D-MEM supplemented with hypoxanthine, aminopterin, thymidine, 10% fetal bovine serum and 10% NCTC-109 media supplement (Gibco-BRL). The fusion efficiencies (wells with colony growth vs. number of wells seeded) were 26.4% (119/450) and 76.4% (346/450), respectively. Reactivity was evaluated by SDS-PAGE Western blots, Dot blots and ELISAs using the NucA protein and whole cells. Positive reactors were identified, designated 1–25, coded Nt63 (first fusion) or Nt63/2 (second fusion) and saved for further characterization.

Selected hybridomas of interest were subcloned once by limiting dilution procedure. Monoclonal antibodies were provided as tissue culture supernatant (TCS), concentrated by 50% saturated ammonium sulfate precipitation (SAS-TCS) or ascites.

Generation of Polyclonal sera Polyclonal sera was generated in New Zealand white rabbits. Six rabbits were screened for background titers using P860295 whole cell ELISA. Two rabbits with the lowest titers were picked for immunization with nNucA protein at 25 µg per dose plus 25 µg MPL™ in saline at weeks 0, 4 and 8. Rabbits were exsanguinated at week 10. Protein was purified as described above and run on a 12% SDS-PAGE gel to increase the purity from its approximately 90% level. The 63 kD band was cut out of the Coomassie stained gel and serially passed through 18G, 20G and 22G needles. The adjuvant MPL™ in 0.9% saline was added and 0.2 ml was injected into the rabbits. The polyclonal sera gave a high background in colony blots even after absorption to XL1-Blue MRF', Y1090R⁻, Y1089R⁻ and Y1088 cells.

Immunogenicity studies Immunogenicity studies conducted on nNucA and rNucA are summarized in Tables 2–6 below. Pooled sera were assayed for antibody titers to nNucA and/or rNucA, whole cell titers to several heterologous NTHi strains and also bactericidal titers to mainly P861454.

Table 2 sets forth the dosages used in the immunogenicity studies.

TABLE 2

Dosages in Immunogenicity studies

| study# | antigen | dose | adjuvant | dose | species mouse | #mice |
|---|---|---|---|---|---|---|
| #1 | | | | | | |
| E547 | nucA | 1 μg x2 | MPL ™ | 50 μg | Swiss- | 5 |
| E548 | " | 5 μg x2 | MPL ™ | 50 μg | Webster | 5 |
| E549 | " | 10 μg x2 | MPL ™ | 50 μg | " | 5 |
| E550 | " | 20 μg x2 | MPL ™ | 50 μg | " | 5 |
| #2 | | | | | | |
| N085 | nNucA | 5 μg x2 | none | | BALB/c | 5 |
| N086 | " | 10 μg x2 | none | | BALB/c | 5 |
| N087 | " | 5 μg x2 | MPL ™ | 50 μg | BALB/c | 5 |
| N088 | " | 5 μg x2 | QS-21 | 20 μg | BALB/c | 5 |
| N089 | rNucA | 5 μg x2 | none | | BALB/c | 5 |
| N090 | " | 10 μg x2 | none | | BALB/c | 5 |
| N091 | " | 5 μg x2 | MPL ™ | 50 μg | BALB/c | 5 |
| N092 | " | 5 μg x2 | QS-21 | 20 μg | BALB/c | 5 |

TABLE 2-continued

Dosages in Immunogenicity studies

| study# | antigen | dose | adjuvant | dose | species mouse | #mice |
|---|---|---|---|---|---|---|
| #3 | | | | | | |
| N710 | rNucA | 1 μg x3 | MPL ™ | 50 μg | BALB/c | 10 |
| N711 | " | 5 μg x3 | MPL ™ | 50 μg | BALB/c | 10 |
| N712 | " | 10 μg x3 | MPL ™ | 50 μg | BALB/c | 10 |
| N713 | nNucA | 5 μg x3 | MPL ™ | 50 μg | BALB/c | 10 |
| N755 | rNucA | 5 μg x3 | MPL ™ | 50 μg | BALB/c | 20 |

MPL ™ in Studies #2 and 3 were made in triethanolamine (TEM).
QS-21 in study #2 was Stimulon ™ QS-21 and was made in PBS, pH 6.
Immunization schedule
Study #1: Vaccinated at weeks 0, 4 and 6. Bled at 0, 4, 6 and 8.
Study #2: Vaccinated at weeks 0 and 4. Bled at 0, 4 and 6.
Study #3: Vaccinated at weeks 0, 4 and 8. Bled at 0, 4, 6 (N755 only), 8 and 10.

Table 3 presents a compilation of whole cell (WC) ELISA data from studies #1 and 3.

Table 4 presents WC ELISA data from study #2, including subtyping of the IgG class of antibodies.

Table 5 presents bactericidal data from studies #1, 2 and 3. Bactericidal titers for study #3 were an average of two assays except for group N755. Immunogenicity study #1 showed that the nNucA protein has the potential to be a vaccine candidate. See Tables 3 and 5. It showed elevated whole cell titers to all heterologous strains tested at the time. More importantly, it showed bactericidal activity for two out of four heterologous strains tested (Table 5). Studies #2 and 3 repeated the whole cell data. See Tables 3 and 4. Bactericidal activity of these sera was shown for two heterologous strains (data for strain P861454 is shown in Table 5). Three other strains were attempted, but due to technical difficulties no data could be reported.

Table 6 presents antibody ELISA titers from these three studies.

TABLE 3

Whole Cell (WC) ELISA

Study #1

| Group | P860295 Week 0 | Week 8 | Group | Week 0 | Week 8 | Week 0 | Week 8 | Week 0 | Week 8 |
|---|---|---|---|---|---|---|---|---|---|
| E547 | | | E548 | P860295 | | P810384 | | P861454 | |
| IgG | 81 | 2,288 | IgG | 28 | 6,309 | 123 | >6,400 | 149 | >6,400 |
| IgM | 273 | 520 | IgM | 188 | 1,432 | 362 | 902 | 463 | 1,286 |
| E549 | | | E548 | P880859 | | N1955 | | DL208 | |
| IgG | 40 | 1,078 | IgG | 75 | >6,400 | 119 | >6,400 | 131 | >6,400 |
| IgM | 246 | 842 | IgM | 276 | 1,498 | 377 | 1,575 | 292 | 1,794 |
| E550 | | | E548 | N830161E | | Whittier | | Eagan | |
| IgG | 32 | 1,867 | IgG | 186 | >6,400 | 112 | >6,400 | <50 | >6,400 |
| IgM | 218 | 663 | IgM | 859 | 1,732 | 294 | 1,856 | 121 | 914 |

Study #3 - IgG Only at Week 0 and Week 10

| Group | P860295 | | P810384 | | P861454 | | P880859 | | TN106 | | DL208 | | Eagan | |
|---|---|---|---|---|---|---|---|---|---|---|---|---|---|---|
| N710 | <300 | 15,803* | <300 | 35,641 | <300 | 21,960 | <300 | 18,102 | <300 | 15,334 | <300 | 22,154* | <300 | + |
| N711 | <300 | 19,842* | <300 | 40,429 | 426 | 26,846 | <300 | 21,075 | <300 | 18,095 | <300 | 23,141 | <300 | + |
| N712 | <300 | 28,600 | <300 | 51,533 | 557 | 29,089 | <300 | 29,256 | <300 | 22,329 | <300 | 30,170 | <300 | + |
| N713 | <300 | 20,954 | <300 | 43,294 | <300 | 23,243 | <300 | 20,058 | <300 | 17,374 | <300 | 28,783 | <300 | + |

TABLE 3-continued

Whole Cell (WC) ELISA

| N755 | <300 | 25,016* | 399 | 37,820 | 2571 | 27,550 | <300 | 19,747 | <300 | 17,673* | 843 | 25,069 | <300 | + |
| Standard | | 807,990 | | 484,188 | | 536,940 | | 341,502 | | 343,730 | | 451,905 | | 268,032 | standard for Study #3 WC ELISA was pooled week 8 mouse sera from E951 immunised with total OMP from P860295.
*Slope used to determine value was <−0.74. Endpoint = 0.1 ELISA data for Eagan: + denotes positive titer, but precise endpoints were not reportable using log-log linear regression analysis due to low titration slopes (< or = −0.5). Antigen on cell may be limiting or inaccessible.

TABLE 4

Whole Cell ELISA on Week 6 Sera
Study #2 ELISA for IgG Endpoint = 0.1

|      | P860295 | P810384 | P861454 | P880859 | N1955  | DL208  | N830161 | Whittier |
|------|---------|---------|---------|---------|--------|--------|---------|----------|
| N085 | <300    | <300    | 759     | <300    | <300   | 485    | 614     |          |
| N086 | 468     | <300    | 683     | <300    | <300   | 395    | 580     |          |
| N087 | 27,315  | 23,458  | 11,426  | 20,216  | 24,555 | 35,347 | 28,054  | 24,370   |
| N088 | 21,310  | 10,501  | 6,858   | 14,436  | 15,748 | 16,942 | 18,033* | 25,681   |
| N089 | <300    | <300    | 431     | <300    | <300   | 395    | 342     |          |
| N090 | 560     | 396     | 785     | 332     | 464    | 752    | 829     |          |
| N091 | 65,162  | 39,747  | 16,837  | 30,517  | 34,366 | 44,550 | 38,783* | 59,511   |
| N092 | 94,764  | 48,336  | 14,812  | 40,890  | 48,068 | 54,622 | 64,439  | 71,444   |
| std  | 727,059 | 827,281 | 610,701 | 595,106 | 570,715| 648,426| 731,630 | 435,025  |

|      | Eagan   | H305    | TN106   | P810568 | P880807 | SH1013  | SH1014  | SH1015  |
|------|---------|---------|---------|---------|---------|---------|---------|---------|
| N085 |         | <300    | <300    | 348     | <300    | <300    | <300    | 302     |
| N086 |         | 313     | <300    | <300    | <300    | <300    | <300    | 352     |
| N087 | 3,394   | 23,992  | 11,471  | 13,089  | 16,778  | 17,173  | 14,174  | 44,479  |
| N088 | 2,135   | 13,411  | 7,258   | 6,584   | 11,552  | 10,963  | 10,117  | 29,648  |
| N089 |         | <300    | <300    | <300    | <300    | <300    | <300    | <300    |
| N090 |         | 317     | <300    | 444     | 377     | 365     | 325     | 802     |
| N091 | 7,219   | 32,013  | 22,358  | 20,794  | 24,244  | 24,290  | 23,161  | 66,544  |
| N092 | 7,907   | 25,625  | 39,077  | 21,386  | 30,571  | 29,462  | 35,277  | 117,618 |
| std  | 372,476 | 775,519 | 689,528 | 523,314 | 404,054 | 793,712 | 438,720 | 471,648 |

*Value based on slope < −0.74
Standard (std) used was pooled week 8 mouse sera from E951 immunized with total OMP from P8602955.
IgG subtype for TN106:

|      | Total IgG | IgG1   | IgG2a  | IgG2b  |
|------|-----------|--------|--------|--------|
| N087 | 11,471    | 2,345  | <300   | 633    |
| N088 | 7,258     | 4,750  | <300   | <300   |
| N091 | 22,358    | 11,076 | *749   | 1,120  |
| N092 | 39,077    | 16,748 | 1,394  | 1,066  |
| std  | 689,528   | 75,602 | 21,876 | 33,747 |

TABLE 5

Bactericidal Assay Titers

| strain    | P860295 |      | P810384 |      | P861454 |      | DL208 |      | N830161E |      |
|-----------|---------|------|---------|------|---------|------|-------|------|----------|------|
| Study #1  | wk 0    | wk 8 | wk 0    | wk 8 | wk 0    | wk 8 | wk 0  | wk 8 | wk 0     | wk 8 |
| E548      | <5      | 10,20| <5      | 20,40| <5      | 5    | <5    | <5   | 20       | >640 |
| Study #2  |         |      |         |      | wk 0    | wk 6 |       |      |          |      |
| N085      |         |      |         |      | 23      | 25   |       |      |          |      |
| N086      |         |      |         |      | 11      | 26   |       |      |          |      |
| N087      |         |      |         |      | 12      | 62   |       |      |          |      |
| N088      |         |      |         |      | 14      | 15   |       |      |          |      |
| N089      |         |      |         |      | 15      | 34   |       |      |          |      |
| N090      |         |      |         |      | 20      | 17   |       |      |          |      |
| N091      |         |      |         |      | 17      | 105  |       |      |          |      |
| N092      |         |      |         |      | 26      | 25   |       |      |          |      |

TABLE 5-continued

Bactericidal Assay Titers

| strain | P860295 | P810384 | P861454 | | DL208 | N830161E |
|---|---|---|---|---|---|---|
| | | | wk 0 | wk 10 | | |
| Study #3 | | | | | | |
| N710 | | | <10 | 101 | | |
| N711 | | | 13 | 66.5 | | |
| N712 | | | <10 | 67.1 | | |
| N713 | | | 12 | 118.2 | | |
| N755 | | | <10 | 39 | | |

TABLE 6

Antibody ELISA

| Study #1 | | | | | Study #2 | | | | Study #3 | | |
|---|---|---|---|---|---|---|---|---|---|---|---|
| | IgG ELISA | | IgM ELISA | | | IgG ELISA | | | | IgG ELISA | |
| Group | week 0 nNucA | week 8 nNucA | week 0 nNucA | week 8 nNucA | Group | week 0 n&rNuc | week 6 nNucA | week 6 rNucA | Group | week 0 rNucA | week 10 rNucA |
| E547 | <50 | 215,994 | <50 | <1000 | N085 | <50 | 5,797 | 6,861 | N710 | <50 | 1,721,270 |
| E548 | <50 | 548,951 | 68 | <1000 | N086 | <50 | 4,178 | 5,941 | N711 | <50 | 932,443 |
| E549 | <50 | 165,813 | 85 | <1000 | N087 | <50 | 1,819,468 | 1,372,302 | N712 | <50 | 982,926 |
| E550 | <50 | 784,070 | <50 | <1000 | N088 | <50 | 933,209 | 687,585 | N713 | <50 | 959,983 |
| | | | | | N089 | <50 | 10,079 | 23,329 | N755 | <50 | 1,598,404 |
| | | | | | N090 | <50 | 19,779 | 30,351 | | | |
| | | | | | N091 | <50 | 1,295,759 | 1,025,998 | | | |
| | | | | | N092 | <50 | 2,928,898 | 1,699,462 | | | |

The results of the data set forth in Tables 2–6 will now be presented. Study #1 Study #1 was performed with nNucA protein, isolated and purified as described in Example 1. Four groups of Swiss-Webster mice, five mice per group, were immunized with either 1, 5, 10 or 20 μg of nNucA per mouse at weeks 0, 4, 6 and 8. The adjuvant used was MPL™, 50 μg per dose. Antibody to nNucA and whole cell titers to the homologous P860295NTHi strain were obtained on pooled sera from all bleeds. Data for weeks 0 and 8 are shown (Tables 3 and 6). Whole cell titers on heterologous strains and bactericidal titers were obtained on group E548, the 5 μg dosage group, which gave the highest whole cell titers to the homologous P860295 strain at both weeks 6 (data not shown) and 8 (Table 3). After the second immunization, both whole cell and purified protein ELISA titers were boosted compared to the initial bleeds (data not shown). Two to three-fold boosts were also observed after the third immunization, except for the 10 μg dosage, which showed a 13-fold increase in ELISA titer. The nNucA protein elicited high whole cell ELISA titers against eight heterologous NTHi clinical isolates (Table 3), demonstrating conserved, surface exposed, epitopes. From this study, 5 μg was chosen as the preferred immunization dose for further experiments. A bactericidal assay was performed using sera from the 5 μg dose (E548) on four heterologous NTHi strains. A significant bactericidal titer is considered a four-fold increase over preimmune levels. Significant bactericidal activity was detected against the homologous P860295 strain, as well as for the heterologous NTHi isolates P810384 and N830161E. The titer against strain P861454 may be significant, but could not be determined in this assay, since the lowest dilution tested was 1:5 and the preimmune sera had no activity at that level (Table 5).
Study #2 Study #2 was performed to compare the immunogenicity of nNucA to rNucA, both with and without adjuvants. Two adjuvants were compared: MPL™ and Stimulon™ QS-21. Five Balb/c mice per group were used for these studies. The NucA proteins used for these studies were purified as described in Example 4 with the nNucA protein KSCN extracted from P860295. Mice were immunized at weeks 0 and 4, and bled at weeks 0, 4, and 6. Sera from week 0 and 6 bleeds were analyzed for ELISA reactive antibodies against both purified nNucA, rNucA, and whole NTHi cells.

Results are shown in Tables 4 and 6. The nNucA and rNucA proteins were not highly immunogenic in the absence of adjuvants. Both proteins elicited high ELISA titers against itself or against the other form of the protein when used with either adjuvant (Table 6). No difference was detected when either nNucA or rNucA was used as the immunizing antigen and the sera reacted against each protein. It thus appears that the rNucA elicits antibodies indistinguishable from those elicited by nNucA. Whole cell ELISA titers for these antisera are shown in Table 4. A total of 16 H. influenzae clinical isolates were examined using these antisera. Only those groups containing adjuvants elicited high titer whole cell reactive antisera. The antisera were broadly cross-reactive across the strains, showing that both purified native and recombinant NucA contain conserved, surface exposed epitopes which elicit antibodies when injected into mice. No significant differences were observed between either adjuvant or protein combination in ability to elicit surface reactive antibodies. Unadjuvanted groups showed background levels of surface reactive antibodies. The subclass distribution of the antibody response to one isolate was determined and the results shown in Table 4. The MPL™ groups appear to have a mixed IgG1, IgG2a/b response, while the Stimulon™ QS-21 adjuvanted native protein was a mostly IgG1 response. In contrast, the Stimulon™ QS-21 rNucA group was a mixed IgG1, IgG2a/b response. However, these responses are only for one experiment and may not represent the expected subclass profile for these adjuvants in additional experiments.

Study #3 Study #3 was performed to look at rNucA dose response when formulated with 50 μg MPL™ per dose and to collect sera for the protection study shown in Table 7 below. The rNucA and nNucA were the same preparations as for study #2. Three groups of 10 mice each were immunized with rNucA at per dose amounts of 1 μg (group N710), 5 μg (group N711) or 10 μg (group N71). An additional group of 20 mice, N755 (about 10 weeks old instead of 6–8 weeks) was added later to the study to provide extra sera for the protection study. A fifth group of 10 mice, N713, was immunized with 5 μg of nNucA. All doses contained 50 μg MPL™ per dose and mice were immunized at weeks 0, 4 and 8. Bleeds were taken at weeks 0, 4, 6 (only N755), 8 and 10. See Table 2 for dosages.

The primary response as shown by the IgG ELISA titers for week 4 sera (data not shown) is affected by the dose of rNucA. The lowest titer was obtained with the lowest rNucA dose group. A two- to three-fold higher titer was obtained from the 5 μg dose group. In turn, the titer for the 10 μg dose group was about twice that for the 5 μg dose. Similar titers were obtained for both the nNucA and rNucA groups at 5 μg dose. N755 gave the highest primary response but the lowest boost, about 45-fold after the second dose. All the other groups boosted about 200-fold after the second dose. Groups N710 and N755 boosted about two- to three-fold after the third dose; groups N711, N712 and N713 actually dropped slightly. All titers were comparable after three immunizations. See Table 6.

All strains at a 10 μg dose gave a small primary WC response. DL208 and P861454 were the only two strains that gave a small primary response to all groups. All titers were comparable after the second and third immunizations. N755 gave a higher primary response with DL208, P810384 and P861454 (which also had a high background), but titers again were comparable after the second and third immunizations. However, the bleed at week 6 showed higher, and in some strains the highest titers, over weeks 8 and 10 for group N755. See Table 3 for weeks 0 and 10 results.

Here, again, the results repeated those of the previous studies which showed the cross-reactivity of the sera to all strains tested, even to the encapsulated Type b Eagan strain. However, a definite titer was not obtained for Eagan, probably due to the presence of the capsule, which may have inhibited accessibility of the antigen on the cell surface.

Bactericidal activity of the antisera from Study #2 was determined against two NTHi strains, TN106 and P861454, both heterologous isolates relative to the source of the nucA gene. All sera except the Stimulon™ QS-21-rNucA group showed bactericidal activity against TN106. Results of the BC assay against P861454 are shown in Table 5. The only groups to show a significant (>4-fold rise) bactericidal titer against P861454 were the MPL™ groups, N091 and N087. Thus, either native or recombinant NucA protein adjuvanted with MPL™ was able to elicit a broadly cross-reactive whole cell ELISA response, high ELISA titers against either protein, and bactericidal activity against heterologous NTHi isolates.

Infant rat protection study Four-day old Sprague-Dawley rats were randomized into 10 groups with a mother in each group of 10 infants. The infants were immunized intraperitoneally (IP) as shown in Table 7:

TABLE 7

Immunization Of Rats

| Group # | Immunization | Dilution |
|---|---|---|
| P168 | Equal volumes of week 0 from Study #3 N710, 711, 712 (mice anti-NucA) | 1:2 |
| P169 | Equal volumes of week 10 from Study #3 N710, 711, 712 (mice anti-NUCA) | 1:2 |
| P170 | Same as for P169 but different dilution | 1:5 |
| P171 | Same as for P169 but different dilution | 1:10 |
| P174 | Week 0 from Study #5 (rabbit anti-HiPal) | 1:5 |
| P175 | Week 13 from Study #5 (rabbit anti-HiPal) | 1:5 |
| P176 | E117-5 Mab to PRP, ascites lot 091994 | 1:10 |
| P177 | PCM buffer control | |

Groups P174 and P175 received anti-sera from rabbits immunized with a 16 kD NTHi protein designated P6 (also known as HiPAL or PBOMP-1 (22)). Group P176 received a monoclonal antibody raised against NTHi polyribosyl ribitol phosphate (PRP). Group P177 received PCM buffer (10 mM $NaPO_4$, pH 7.4, 150 mM NaCl, 0.5 mM $MgCl_2$, 0.15 mM $CaCl_2$) as a buffer control. All dilutions of sera and cells were done in PCM buffer. About 23 hours later, they were challenged IP with 49.5 organisms (0.1 ml) of virulent H. influenzae type b, Eagan strain. Then, 20–24 hours post-challenge, the infant rats were bled and plated for bacterial counts. Tails were nicked and 10 μl blood taken up with a P20 Rainin Pipetman and diluted into 90 μl PCM buffer at RT. Dilutions were vortexed and held at 4° C. until further dilutions were made and 10 μl of each dilution was plated onto chocolate agar in duplicate. Plates were incubated in 5% $CO_2$ incubator at 36.5° C. overnight. The results of the protection study are set forth in Table 8:

TABLE 8

Infant rat protection study

| Group | Anti-Sera to | Species | Dilution | $GMT^1$ (cfu/ul blood) | $GMT^2$ (cfu/ul blood) | p value |
|---|---|---|---|---|---|---|
| P168 | wk 0, rNucA | mouse | 2-fold | 3785.9 | 4409.9 | |
| P169 | wk 10, rNucA | mouse | 2-fold | 395.6 | 455.5 | 0.0155/0.0191 |
| P170 | wk 10, rNucA | mouse | 5-fold | 2271.2 | 2190.7 | 1.000/0.4495 |
| P171 | wk 10, rNucA | mouse | 10-fold | 3368.0 | 2867.2 | 1.000/0.7623 |
| P174 | wk 0, HiPal | rabbit | 5-fold | 298.8 | 264.9 | |
| P175 | wk 13, HiPal | rabbit | 5-fold | 0.5 | 0.5 | |

TABLE 8-continued

Infant rat protection study

| Group | Anti-Sera to | Species | Dilution | GMT[1] (cfu/ul blood) | GMT[2] (cfu/ul blood) | p value |
|---|---|---|---|---|---|---|
| P176 | mabE117-5 | ascites | 10-fold | 0.5 | 0.5 | |
| P177 | PCM control | | | 2715.6 | 3037.2 | |

[1]Geometric-Mean Titers (GMTs) were based on equal weighting on all countable plates.
[2]GMTs were based on higher weight being placed on countable lower dilutions.
Countable plates were <500 cfu/plate.
Limit of detection was 100 cfu/ml, plating 10 μl of the dilution.
Plates for groups P175 and P176 were 0 at the lowest dilution so can be anywhere from 0–99 cfu/ml.
Here a nuxnber, 50 cfu/ml, was assigned for the purposes of calculating geometric mean (GMT).
Plates that were too many to count even at the highest dilution were also assigned numbers based on estimates:
> = 1000 cfu/plate
>> = 2000 cfu/plate
lawn = 6000 cfu/plate
p value: Kruskal-Wallis is a conservative P value test used when sample values cover a large range.
It is not as sensitive to very large values. P values <0.05 are statistically significant with this test.

The infant rat animal model for Hib meningitis demonstrates the ability of antibodies to reduce bacteremia (and subsequent death) due to Hib. Rabbit sera in general gives some nonspecific immunity to Hib in the blood of infant rats, as can be seen when comparing the week 0 cfus of the mouse and rabbit antisera. The model thus uses preimmune rabbit sera as the negative control for the immune rabbit sera. As expected, rabbit control antisera against the P6 protein decreased the GMT of Hib in the blood of rats from 300 to 0.5, thus showing reduced bacteremia, as did the mouse monoclonal antibody against the PRP capsule of Hib (Group P176). Mouse anti-rNucA sera, at a 1:2 dilution, significantly reduced levels of bacteremia compared to week 0 (preimmune) sera, showing a positive result in this animal model and the ability to opsonize encapsulated Hib. These results demonstrate the effectiveness of the anti-rNucA sera in this model and its vaccine potential against *Haemophilus influenzae*.

Example 8

Specificity Of The nucA 420 bp Probe

The 420 bp DNA probe described above was tested for its specificity in identifying Haemophilus species. The probe was used in Southern hybridizations to generate a partial restriction map of the nucA gene and in dot blot hybridization for identification of the Haemophilus species. Cultures were grown to $O.D._{600}$ of about 1.0 and stored at −20° C. Five ul of culture was spotted onto a dry Hybond-N membrane with a 3 mm Whatman paper underneath for blotting off excess fluid. The membrane was air dried for about 10 minutes. It was lysed in 10% SDS, then denatured in denaturing buffer (1.5M NaCl, 0.5M NaOH) for 7 minutes at RT. Excess buffer was blotted off with 3 mm Whatman paper. The membrane was neutralized in neutralizing buffer (1.5M NaCl, 0.5M Tris-HCl, pH 7.2, 1 mM EDTA) for 3 minutes at RT. The membrane was placed on 3 mm Whatman paper to blot off excess buffer and the neutralization treatment repeated. The membrane was rinsed in 2× SSC and air dried on 3 mm Whatman paper. The DNA was cross-linked to the membrane using a Stratagene UV crosslinker in the auto mode. The membrane was prehybridized in prehybridization buffer (5× SSC, 1.0% Blocking reagent, 0.1% N-lauroylsarcosine, 0.02% SDS) at 65° C. for 2–4 hours. Hybridization was performed in prehybridization buffer plus probe (PCR dig-dUTP labelled P860295 chromosomal DNA with specific primers giving the same 420 bp fragment as described above) at 65° C. overnight. Two washes were performed in 2× SSC-0.1% SDS at 65° C. for 5–15 minutes. Another two washes were performed in 0.1× SSC-0.1% SDS at 65° C. for 15 minutes. The membrane was developed according to the Genius™ kit protocol (Boehringer Mannheim).

Listed below are the species and strains of cell cultures that were spotted for dot hybridization with this nucA probe. All the Haemophilus strains were visually positive including type b, Eagan strain. The only non-Haemophilus species that was positive was the *E. coli* culture containing the rnucA plasmid, pPX691. All the other species were negative for the probe. See FIG. 15.

1. E. coli InvaF'
2. pTrcHisC in InvaF'
3. pPX691 in InvaF'
4. NTHi P810384
5. NTHi P810568
6. NTHi P860295
7. NTHi P861454
8. NTHi P880859
9. NTHi DL208
10. NTHi H305
11. NTHi N1955
12. NTHi N830161E
13. NTHi SH1013
14. NTHi SH1014
15. NTHi SH1015
16. NTHi TN106
17. Hib Eagan
18. GC LB2
19. GC Pgh3-2
20. H. pylori
21. M. catarrhalis 035e
22. S. typhimurium 3261

GC for 18. and 19. is *Neisseria gonorrhoeae*. These results demonstrated the specificity of the probe for nucA sequences.

Example 9

Conservation Of The NucA Sequence Among *H. influenzae*

Total cell lysates from several NTHi strains and type b, Eagan strain, were analyzed on Westerns probed with Mab Nt63-34-25 or rabbit polyclonals, both to nNucA. All strains tested showed a conserved 63 kD band (by size on an SDS-PAGE gel) with the nNucA antisera (data not shown). Several NTHi strains and type b, Eagan and Whittier strains, were also grown up to O.D.$_{490}$ of about 1.0, fixed with 0.4% formaldehyde, diluted to O.D.$_{620}$ of about 0.2 in PBS and coated onto plates by drying for WC ELISA. See Tables 3 and 4. All strains tested showed an elevated titer on the WC ELISA.

As described above, the sequence of the NucA protein was obtained from strain P860295 (SEQ ID NO:2). Next, the nucA fragment (with or without signal sequence) was amplified out of eight other NTHi genomes and the type b, Eagan strain, using primers made in sequencing the nucA region from the P860295 genome. The PCR fragments were cloned into PCR™II and sequenced. Complete sequences of the mature nucA gene region were obtained for strains P810384, P810568, P861454, P880859, N1955, TN106, SH1014, SH1015 and Eagan. A protein alignment was generated from the deduced amino acid sequences of the mature NucA protein, including that of P860295. Four of the strains (P880859, TN106, SH1015 and Eagan) are 100% identical to P860295. The other strains differ from P860295 by one to seven amino acid residues (see Table 9). This shows the considerable extent to which the nucA gene is conserved among the *H. influenzace* strains tested.

TABLE 9

Mature NucA Amino Acid Residue Differences Between Strain P860295 And Other H. influenzae Strains

| P810568 | P861454 | P810384 | N1955 | SH1014 |
|---------|---------|---------|-------|--------|
| K79E | K79E | | | |
| | N186K | | | |
| S262G | S262G | | | |
| V294A | | | | |
| E305Q | E305Q | | | |
| K327R | | | | |
| T337A | T337A | | | |
| | | D360Y | D360Y | |
| R376H | R376H | | | |
| | | | | V436I |

Bibliography

1. Moxon, E. R., *J. Antimicrob. Chemother.*, 18 Supp. A, 17–24 (1986).

2. Murphy, T. F., and Apicella, M. A., *Rev. Infect. Dis.*, 9, 1–15 (1987).

3. Sambrook, J., et al., *Molecular Cloning: A Laboratory Manual*, 2nd ed., Cold Spring Harbor Laboratory Press, Cold Spring Harbor, N.Y. (1989).

4. Barenkamp, S. J., et al., *Infect. Immun.*, 52, 572–578 (1986).

5. Moxon, E. R., et al., *J. Infect. Dis.*, 136, S186–190 (1977).

6. Lam, J. S., et al., *Current Microbiol.*, 3, 359–364 (1980).

7. Ulmer, J. B., et al., *Science*, 2, 1745–1749 (1993).

8. Fynan, E. F., et al., *Proc. Nat'l. Acad. Sci. USA*, 9, 11478–11482 (1993).

9. Silhavy, T., et al., *Experiments With Gene Fusions*, pages 95–96, Cold Spring Harbor Laboratory Press, Cold Spring Harbor, N.Y. (1984).

10. Faure, D., *BioTechniques*, 13, 22–26 (1992).

11. Sprengart, M. L., et al., *Nuc. Acids Res.*, 18, 1719–1723 (1990).

12. Luzio, J. P., et al., pages 111–138, Kenny, A. J., and Turner, A. J., eds., in *Mammalian Ectoenzymes*, (Elsevier, Amsterdam (1987).

13. Glaser, L., et al., *J. Biol. Chem.*, 242, 1944–1954 (1967).

14. Neu, H. C., *J. Biol. Chem.*, 242, 3896–3904 (1967).

15. Burns, D. M., and Beacham, I. R., *Nuc. Acids Res.*, 14, 4325–4342 (1986).

16. Bengis-Garber, C., *Can. J. Microbiol.*, 31, 543–548 (1985).

17. Tamao, Y., et al., *J. Biochem.*, 109, 24–29 (1991).

18. Maznitsa. I. I., et al., *FEMS Microbiology Letters*, 7, 173–176 (1990).

19. Misumi, Y., et al., *J. Biol. Chem.*, 265, 2178–2183 (1990).

20. Ikehara, Y., et al., *Biochimica et Biophysica Acta*, 470, 202–211 (1977).

21. Chen, P. S., et al., *Analytical Chem.*, 28, 1756–1758 (1956).

22. U.S. Pat. No. 5,110,908.

What is claimed is:

1. An isolated and purified DNA sequence comprising a DNA sequence encoding the NucA protein of *Haemophilus influenzae* (*H. influenzae*), where said NucA protein has:
   (a) a molecular weight of approximately 63,000 Daltons as measured on a 12% SDS-PAGE gel; and
   (b) 5'-nucleotidase activity.

2. The isolated and purified DNA sequence of claim 1, wherein said DNA sequence hybridizes under high stringency Southern hybridization conditions with a DNA Sequence encoding the NucA protein of *H. influenzae* having the amino acid sequence of amino acids 26–603 of SEQ ID NO:2.

3. The isolated and purified DNA Sequence of claim 1, wherein said DNA sequence hybridizes under high stringency Southern hybridization conditions with a DNA sequence having the nucleotide sequence of nucleotides 304–2037 of SEQ ID NO:1.

4. The isolated and purified DNA sequence of claim 2, wherein the DNA sequence hybridizes under high stringency Southern hybridization conditions with a DNA sequence encoding the NucA protein of *H. influenzae*, wherein the amino acid sequence of amino acids 26–603 of SEQ ID NO:2 is modified by one or more of the following amino acid residue changes selected from the group consisting of lysine$^{79}$ to glutamic acid, asparagine$^{186}$ to lysine, serine$^{262}$ to glycine, valine$^{294}$ to alanine, glutamic acid$^{305}$ to glutamine, lysine$^{327}$ to arginine, threonine$^{337}$ to alanine, aspartic acid$^{360}$ to tyrosine, arginine$^{376}$ to histidine or valine$^{436}$ to isoleucine.

5. A plasmid containing an isolated and purified DNA sequence of *H. influenzae* comprising the DNA sequence of claim 1.

6. The plasmid of claim 5 wherein the plasmid contains a DNA sequence which hybridizes under high stringency Southern hybridization conditions with a DNA sequence encoding the NucA protein of *H. influenace* having the amino acid sequence of amino acids 26–603 of SEQ ID NO:2.

7. The plasmid of claim 5 wherein the plasmid contains a DNA sequence which hybridizes under high stringency Southern hybridization conditions with a DNA sequence having the nucleotide sequence of nucleotides 304–2037 of SEQ ID NO:1.

8. The plasmid of claim 6 wherein the plasmid contains a DNA sequence which hybridizes under high stringency Southern hybridization conditions with a DNA sequence which encodes the NucA protein of *H. influenzae*, wherein the amino acid sequence of amino acids 26–603 of SEQ ID NO:2 is modified by one or more of the following amino acid residue changes selected from the group consisting of lysine$^{79}$ to glutamic acid, asparagine$^{186}$ to lysine, serine$^{262}$ to glycine, valine$^{294}$ to alanine, glutamic acid$^{305}$ to glutamine, lysine$^{327}$ to arginine, threonine$^{337}$ to alanine, aspartic acid$^{360}$ to tyrosine, arginine$^{376}$ to histidine or valine$^{436}$ to isoleucine.

9. The plasmid of claim 7 wherein the plasmid is that designated pPX691 (ATCC 98104).

10. A host cell transformed with the plasmid of claim 5.

11. The host cell of claim 10 wherein the host cell is *Escherichia coli* strain InvaF'.

12. The host cell of claim 11 wherein the plasmid is that designated pPX691 (ATCC 98104).

13. A method of producing the NucA protein of *H. influenzae* which comprises transforming or transfecting a host cell with the plasmid of claim 5 and culturing the host cell under conditions which permit the expression of said NucA protein by the host cell.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 2263 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 229..2037

(xi) SEQUENCE DESCRIPTION: SEQ ID NO:1:

```
TGTTGACAAT TAATCATCCG GCTCGTATAA TGTGTGGAAT TGTGAGCGGA TAACAATTTC        60

ACACAGGAAA CAGCGCCGCT GAGAAAAAGC GAAGCGGCA  TGCTCTTTAA CAATTTATCA       120

GACAATCTGT GTGGGCACTC GGCCGGAATT ATCGATTAAC TTTATTATTA AAAATTAAAG       180

AGGTATATAT TAATGTATCG ATTAAATAAG GAGGAATAAA CCATGGGT ATG CTT TTA        237
                                                    Met Leu Leu
                                                     1
```

| | | | | | | | | | | | | | | | | |
|---|---|---|---|---|---|---|---|---|---|---|---|---|---|---|---|---|
| TCC | AAA | AAA | TCA | GCT | ACC | TTT | GCA | CTC | AGT | GTA | TTT | GCG | ATG | CTT | TTC | 285 |
| Ser | Lys | Lys | Ser | Ala | Thr | Phe | Ala | Leu | Ser | Val | Phe | Ala | Met | Leu | Phe | |
| | 5 | | | | 10 | | | | | 15 | | | | | | |
| ACT | AGT | GTA | GCT | CTT | GCC | AAA | GAG | GCA | CCA | CAA | GCT | CAC | AAA | GCT | GTG | 333 |
| Thr | Ser | Val | Ala | Leu | Ala | Lys | Glu | Ala | Pro | Gln | Ala | His | Lys | Ala | Val | |
| 20 | | | | | 25 | | | | | 30 | | | | | 35 | |
| GAA | TTA | AGT | ATT | TTG | CAC | ATC | AAT | GAT | CAC | CAT | TCT | TAT | TTA | GAA | CCG | 381 |
| Glu | Leu | Ser | Ile | Leu | His | Ile | Asn | Asp | His | His | Ser | Tyr | Leu | Glu | Pro | |
| | | | | 40 | | | | | 45 | | | | | 50 | | |
| CAC | GAA | ACA | CGG | ATT | AAT | TTA | AAT | GGT | CAG | CAA | ACC | AAA | GTG | GAT | ATT | 429 |
| His | Glu | Thr | Arg | Ile | Asn | Leu | Asn | Gly | Gln | Gln | Thr | Lys | Val | Asp | Ile | |
| | | | 55 | | | | | 60 | | | | | 65 | | | |
| GGT | GGT | TTT | TCT | GCT | GTC | AAT | GCA | AAA | CTT | AAC | AAA | TTG | CGT | AAA | AAA | 477 |
| Gly | Gly | Phe | Ser | Ala | Val | Asn | Ala | Lys | Leu | Asn | Lys | Leu | Arg | Lys | Lys | |
| | | 70 | | | | | 75 | | | | | 80 | | | | |
| TAC | AAA | AAT | CCA | TTA | GTA | CTG | CAT | GCA | GGC | GAT | GCC | ATT | ACT | GGT | ACG | 525 |
| Tyr | Lys | Asn | Pro | Leu | Val | Leu | His | Ala | Gly | Asp | Ala | Ile | Thr | Gly | Thr | |
| | 85 | | | | | 90 | | | | | 95 | | | | | |
| CTT | TAC | TTC | ACG | CTG | TTT | GGT | GGT | TCT | GCA | GAT | GCA | GCT | GTG | ATG | AAC | 573 |
| Leu | Tyr | Phe | Thr | Leu | Phe | Gly | Gly | Ser | Ala | Asp | Ala | Ala | Val | Met | Asn | |
| 100 | | | | | 105 | | | | | 110 | | | | | 115 | |
| GCA | GGT | AAT | TTT | CAT | TAT | TTT | ACT | TTA | GGT | AAT | CAT | GAA | TTT | GAC | GCG | 621 |
| Ala | Gly | Asn | Phe | His | Tyr | Phe | Thr | Leu | Gly | Asn | His | Glu | Phe | Asp | Ala | |
| | | | | 120 | | | | | 125 | | | | | 130 | | |
| GGT | AAT | GAA | GGG | TTA | TTA | AAA | CTG | CTT | GAA | CCA | TTA | AAA | ATC | CCT | GTG | 669 |
| Gly | Asn | Glu | Gly | Leu | Leu | Lys | Leu | Leu | Glu | Pro | Leu | Lys | Ile | Pro | Val | |
| | | | 135 | | | | | 140 | | | | | 145 | | | |
| CTT | TCA | GCT | AAT | GTG | ATT | CCT | GAT | AAA | AGT | TCA | ATT | TTG | TAT | AAC | AAA | 717 |
| Leu | Ser | Ala | Asn | Val | Ile | Pro | Asp | Lys | Ser | Ser | Ile | Leu | Tyr | Asn | Lys | |
| | | 150 | | | | | 155 | | | | | 160 | | | | |
| TGG | AAA | CCT | TAC | GAT | ATT | TTC | ACT | GTG | GAT | GGA | GAA | AAA | ATT | GCC | ATC | 765 |
| Trp | Lys | Pro | Tyr | Asp | Ile | Phe | Thr | Val | Asp | Gly | Glu | Lys | Ile | Ala | Ile | |
| | 165 | | | | | 170 | | | | | 175 | | | | | |
| ATC | GGT | TTA | GAT | ACC | GTG | AAT | AAA | ACA | GTG | AAT | TCC | TCT | TCA | CCA | GGT | 813 |
| Ile | Gly | Leu | Asp | Thr | Val | Asn | Lys | Thr | Val | Asn | Ser | Ser | Ser | Pro | Gly | |
| 180 | | | | | 185 | | | | | 190 | | | | | 195 | |
| AAG | GAT | GTG | AAG | TTC | TAT | GAT | GAA | ATT | GCT | ACC | GCA | CAA | ATT | ATG | GCA | 861 |
| Lys | Asp | Val | Lys | Phe | Tyr | Asp | Glu | Ile | Ala | Thr | Ala | Gln | Ile | Met | Ala | |
| | | | | 200 | | | | | 205 | | | | | 210 | | |
| AAT | GCG | CTA | AAA | CAG | CAA | GGA | ATT | AAT | AAA | ATT | ATC | CTA | CTT | TCA | CAC | 909 |
| Asn | Ala | Leu | Lys | Gln | Gln | Gly | Ile | Asn | Lys | Ile | Ile | Leu | Leu | Ser | His | |
| | | | 215 | | | | | 220 | | | | | 225 | | | |
| GCA | GGT | AGT | GAA | AAA | AAT | ATC | GAA | ATT | GCT | CAA | AAA | GTA | AAT | GAT | ATT | 957 |
| Ala | Gly | Ser | Glu | Lys | Asn | Ile | Glu | Ile | Ala | Gln | Lys | Val | Asn | Asp | Ile | |
| | | 230 | | | | | 235 | | | | | 240 | | | | |
| GAT | GTG | ATC | GTT | ACT | GGC | GAT | TCA | CAT | TAT | TTA | TAC | GGA | AAT | GAT | GAA | 1005 |
| Asp | Val | Ile | Val | Thr | Gly | Asp | Ser | His | Tyr | Leu | Tyr | Gly | Asn | Asp | Glu | |
| | 245 | | | | | 250 | | | | | 255 | | | | | |
| TTA | CGT | AGT | TTA | AAA | CTT | CCA | GTA | ATC | TAT | GAA | TAT | CCA | CTT | GAA | TTT | 1053 |
| Leu | Arg | Ser | Leu | Lys | Leu | Pro | Val | Ile | Tyr | Glu | Tyr | Pro | Leu | Glu | Phe | |
| 260 | | | | | 265 | | | | | 270 | | | | | 275 | |

```
AAA AAT CCA AAT GGA GAG CCT GTA TTT GTA ATG GAA GGC TGG GCT TAT     1101
Lys Asn Pro Asn Gly Glu Pro Val Phe Val Met Glu Gly Trp Ala Tyr
            280                 285                 290

TCT GCC GTG GTG GGG GAT TTA GGT GTT AAA TTC AGC CCT GAA GGT ATA     1149
Ser Ala Val Val Gly Asp Leu Gly Val Lys Phe Ser Pro Glu Gly Ile
            295                 300                 305

GCG TCT ATT ACT CGT AAA ATT CCT CAC GTG TTA ATG AGT TCT CAT AAA     1197
Ala Ser Ile Thr Arg Lys Ile Pro His Val Leu Met Ser Ser His Lys
            310                 315                 320

CTT CAA GTG AAA AAT TCG GAA GGT AAA TGG GCT GAA TTA ACT GGC GAT     1245
Leu Gln Val Lys Asn Ser Glu Gly Lys Trp Ala Glu Leu Thr Gly Asp
            325                 330                 335

GAA CGT AAA AAA GCA CTT GAT ACT TTA AAA TCA ATG AAA AGT ATT TCA     1293
Glu Arg Lys Lys Ala Leu Asp Thr Leu Lys Ser Met Lys Ser Ile Ser
340                 345                 350                 355

CTT GAT GAT CAC GAT GCA AAA ACC GAT AAG CTT ATT GCT AAA TAT AAA     1341
Leu Asp Asp His Asp Ala Lys Thr Asp Lys Leu Ile Ala Lys Tyr Lys
            360                 365                 370

AGT GAA AAA GAT CGC TTA GCA CAA GAA ATT GTG GGC GTT ATC ACT GGT     1389
Ser Glu Lys Asp Arg Leu Ala Gln Glu Ile Val Gly Val Ile Thr Gly
            375                 380                 385

TCT GCA ATG CCG GGC GGT TCA GCA AAC CGT ATC CCA AAT AAA GCA GGA     1437
Ser Ala Met Pro Gly Gly Ser Ala Asn Arg Ile Pro Asn Lys Ala Gly
            390                 395                 400

TCT AAT CCA GAA GGT TCT ATT GCA ACG CGT TTT ATT GCA GAA ACA ATG     1485
Ser Asn Pro Glu Gly Ser Ile Ala Thr Arg Phe Ile Ala Glu Thr Met
            405                 410                 415

TAT AAC GAA CTC AAA ACA GTG GAT TTA ACT ATT CAA AAT GCT GGC GGT     1533
Tyr Asn Glu Leu Lys Thr Val Asp Leu Thr Ile Gln Asn Ala Gly Gly
420                 425                 430                 435

GTA CGC GCA GAT ATT TTA CCG GGT AAT GTA ACC TTT AAC GAT GCT TAT     1581
Val Arg Ala Asp Ile Leu Pro Gly Asn Val Thr Phe Asn Asp Ala Tyr
            440                 445                 450

ACT TTC TTA CCT TTC GGA AAT ACG TTA TAT ACC TAT AAA ATG GAA GGT     1629
Thr Phe Leu Pro Phe Gly Asn Thr Leu Tyr Thr Tyr Lys Met Glu Gly
            455                 460                 465

TCG TTA GTG AAA CAA GTG CTT GAA GAT GCA ATG CAA TTT GCT TTG GTT     1677
Ser Leu Val Lys Gln Val Leu Glu Asp Ala Met Gln Phe Ala Leu Val
            470                 475                 480

GAT GGC TCT ACA GGT GCA TTC CCT TAT GGT GCA GGT ATT CGT TAT GAA     1725
Asp Gly Ser Thr Gly Ala Phe Pro Tyr Gly Ala Gly Ile Arg Tyr Glu
            485                 490                 495

GCG AAT GAA ACA CCA AAT GCG GAA GGT AAG CGT TTA GTG AGT GTT GAA     1773
Ala Asn Glu Thr Pro Asn Ala Glu Gly Lys Arg Leu Val Ser Val Glu
500                 505                 510                 515

GTC TTG AAT AAA CAA ACC CAA CAA TGG GAA CCG ATT GAT GAT AAC AAA     1821
Val Leu Asn Lys Gln Thr Gln Gln Trp Glu Pro Ile Asp Asp Asn Lys
            520                 525                 530

CGT TAT CTT GTC GGA ACA AAT GCT TAT GTT GCA GGT GGT AAA GAC GGT     1869
Arg Tyr Leu Val Gly Thr Asn Ala Tyr Val Ala Gly Gly Lys Asp Gly
            535                 540                 545

TAT AAA ACC TTT GGT AAA TTA TTT AAC GAT CCA AAA TAT GAA GGC GTT     1917
Tyr Lys Thr Phe Gly Lys Leu Phe Asn Asp Pro Lys Tyr Glu Gly Val
            550                 555                 560

GAT ACC TAC TTG CCT GAT GCA GAA AGT TTC ATA AAA TTT ATG AAA AAA     1965
Asp Thr Tyr Leu Pro Asp Ala Glu Ser Phe Ile Lys Phe Met Lys Lys
            565                 570                 575

CAT CCG CAC TTT GAG GCT TAC ACT TCA TCA AAT GTG AAA TTT AAT GCT     2013
His Pro His Phe Glu Ala Tyr Thr Ser Ser Asn Val Lys Phe Asn Ala
580                 585                 590                 595
```

```
TCA ACT GAT GCA TTA CCT AAA AAA TAAAATTGAA AAATAGGCTA AAAATAGCGC    2067
Ser Thr Asp Ala Leu Pro Lys Lys
                        600

GTATTTAACG CGCTATTTTT GTTATTAGTC CTAGGTTTGA AGACTTCAGG ATCCGACCTC    2127

GAGATCTGCA GATGGTACCA TATGGGAATT CGAAGCTTGG CTGTTTTGGC GGATGAGAGA    2187

AGATTTTCAG CCTGATACAG ATTAAATCAG AACGCAGAAG CGGTCTGATA ACAGAATTTG    2247

CCTGGCGGCA GTAGCG                                                    2263
```

(2) INFORMATION FOR SEQ ID NO:2:

(i) SEQUENCE CHARACTERISTICS:
        (A) LENGTH: 603 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Leu Ser Lys Lys Ser Ala Thr Phe Ala Leu Ser Val Phe Ala
 1               5                  10                  15

Met Leu Phe Thr Ser Val Ala Leu Ala Lys Glu Ala Pro Gln Ala His
                20                  25                  30

Lys Ala Val Glu Leu Ser Ile Leu His Ile Asn Asp His His Ser Tyr
            35                  40                  45

Leu Glu Pro His Glu Thr Arg Ile Asn Leu Asn Gly Gln Gln Thr Lys
        50                  55                  60

Val Asp Ile Gly Gly Phe Ser Ala Val Asn Ala Lys Leu Asn Lys Leu
65                  70                  75                  80

Arg Lys Lys Tyr Lys Asn Pro Leu Val Leu His Ala Gly Asp Ala Ile
                85                  90                  95

Thr Gly Thr Leu Tyr Phe Thr Leu Phe Gly Ser Ala Asp Ala Ala
            100                 105                 110

Val Met Asn Ala Gly Asn Phe His Tyr Phe Thr Leu Gly Asn His Glu
        115                 120                 125

Phe Asp Ala Gly Asn Glu Gly Leu Leu Lys Leu Leu Glu Pro Leu Lys
    130                 135                 140

Ile Pro Val Leu Ser Ala Asn Val Ile Pro Asp Lys Ser Ser Ile Leu
145                 150                 155                 160

Tyr Asn Lys Trp Lys Pro Tyr Asp Ile Phe Thr Val Asp Gly Glu Lys
                165                 170                 175

Ile Ala Ile Ile Gly Leu Asp Thr Val Asn Lys Thr Val Asn Ser Ser
            180                 185                 190

Ser Pro Gly Lys Asp Val Lys Phe Tyr Asp Glu Ile Ala Thr Ala Gln
        195                 200                 205

Ile Met Ala Asn Ala Leu Lys Gln Gln Gly Ile Asn Lys Ile Ile Leu
    210                 215                 220

Leu Ser His Ala Gly Ser Glu Lys Asn Ile Glu Ile Ala Gln Lys Val
225                 230                 235                 240

Asn Asp Ile Asp Val Ile Val Thr Gly Asp Ser His Tyr Leu Tyr Gly
                245                 250                 255

Asn Asp Glu Leu Arg Ser Leu Lys Leu Pro Val Ile Tyr Glu Tyr Pro
            260                 265                 270

Leu Glu Phe Lys Asn Pro Asn Gly Glu Pro Val Phe Val Met Glu Gly
        275                 280                 285
```

```
Trp Ala Tyr Ser Ala Val Val Gly Asp Leu Gly Val Lys Phe Ser Pro
        290                 295                 300

Glu Gly Ile Ala Ser Ile Thr Arg Lys Ile Pro His Val Leu Met Ser
305                 310                 315                 320

Ser His Lys Leu Gln Val Lys Asn Ser Glu Gly Lys Trp Ala Glu Leu
                325                 330                 335

Thr Gly Asp Glu Arg Lys Lys Ala Leu Asp Thr Leu Lys Ser Met Lys
            340                 345                 350

Ser Ile Ser Leu Asp Asp His Asp Ala Lys Thr Asp Lys Leu Ile Ala
        355                 360                 365

Lys Tyr Lys Ser Glu Lys Asp Arg Leu Ala Gln Glu Ile Val Gly Val
    370                 375                 380

Ile Thr Gly Ser Ala Met Pro Gly Gly Ser Ala Asn Arg Ile Pro Asn
385                 390                 395                 400

Lys Ala Gly Ser Asn Pro Glu Gly Ser Ile Ala Thr Arg Phe Ile Ala
                405                 410                 415

Glu Thr Met Tyr Asn Glu Leu Lys Thr Val Asp Leu Thr Ile Gln Asn
            420                 425                 430

Ala Gly Gly Val Arg Ala Asp Ile Leu Pro Gly Asn Val Thr Phe Asn
        435                 440                 445

Asp Ala Tyr Thr Phe Leu Pro Phe Gly Asn Thr Leu Tyr Thr Tyr Lys
    450                 455                 460

Met Glu Gly Ser Leu Val Lys Gln Val Leu Glu Asp Ala Met Gln Phe
465                 470                 475                 480

Ala Leu Val Asp Gly Ser Thr Gly Ala Phe Pro Tyr Gly Ala Gly Ile
                485                 490                 495

Arg Tyr Glu Ala Asn Glu Thr Pro Asn Ala Glu Gly Lys Arg Leu Val
            500                 505                 510

Ser Val Glu Val Leu Asn Lys Gln Thr Gln Gln Trp Glu Pro Ile Asp
        515                 520                 525

Asp Asn Lys Arg Tyr Leu Val Gly Thr Asn Ala Tyr Val Ala Gly Gly
    530                 535                 540

Lys Asp Gly Tyr Lys Thr Phe Gly Lys Leu Phe Asn Asp Pro Lys Tyr
545                 550                 555                 560

Glu Gly Val Asp Thr Tyr Leu Pro Asp Ala Glu Ser Phe Ile Lys Phe
                565                 570                 575

Met Lys Lys His Pro His Phe Glu Ala Tyr Thr Ser Ser Asn Val Lys
            580                 585                 590

Phe Asn Ala Ser Thr Asp Ala Leu Pro Lys Lys
        595                 600
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AAAGAAGCAC CACAAGCACA TAAA                                  24

(2) INFORMATION FOR SEQ ID NO:4:

(i) SEQUENCE CHARACTERISTICS:
        (A) LENGTH: 24 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

ATTTTACATA TTAATGATCA TCAT                                             24

(2) INFORMATION FOR SEQ ID NO:5:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CCAAAGTGGA TATTGGTG                                                    18

(2) INFORMATION FOR SEQ ID NO:6:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

CATCATAGAA CTTCACATC                                                   19

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GTGAGTGTTG AAGTCTTG                                                    18

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

CGACTCACTA TAGGGAGACC                                                  20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GAAGTCTTCA AACCTAGGAC					20

(2) INFORMATION FOR SEQ ID NO:10:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TATGGCTATG TCTAACATGA CTTACAAACA TCATCATCAT CATCATGGTA TGG					53

(2) INFORMATION FOR SEQ ID NO:11:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTAGCCATAC CATGATGATG ATGATGATGT TTGTAAGTCA TGTTAGACAT AGCCA					55

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GATATCAAAG AAGCTCCTCA AGC					23

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGGATCCT GAAGTCTTCA AACCTAGGAC					30

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGATCCAAAG AAGCTCCTCA AGC					23

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCTACGGCTA GCAAAGAAGC ACCTCAAGC                         29

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

ATTAACCCTC ACTAAAGGGA                               20

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GCTTTCAGCT AATGTGATTC C                              21

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CATCACAGCT GCATCTGCAG                               20

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CTTAATTCCA CAGCTTTGTG AGC                            23

(2) INFORMATION FOR SEQ ID NO:20:

(i) SEQUENCE CHARACTERISTICS:
        (A) LENGTH: 234 base pairs (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 21..227

(xi) SEQUENCE DESCRIPTION: SEQ ID NO:20:

```
TTTAAGAAGG AGATATACAT ATG CGG GGT TCT CAT CAT CAT CAT CAT CAT          50
                     Met Arg Gly Ser His His His His His His
                      1               5                  10

GGT ATG GCT AGC ATG ACT GGT GGA CAG CAA ATG GGT CGG GAT CTG TAC        98
Gly Met Ala Ser Met Thr Gly Gly Gln Gln Met Gly Arg Asp Leu Tyr
             15                  20                  25

GAC GAT GAC GAT AAG GAT CGA TGG ATC CGA CCT CGA GAT CTG CAG CTG       146
Asp Asp Asp Asp Lys Asp Arg Trp Ile Arg Pro Arg Asp Leu Gln Leu
         30                  35                  40

GTA CCA TGG AAT TCG AAG CTT GAT CCG GCT GCT AAC AAA GCC CGA AAG       194
Val Pro Trp Asn Ser Lys Leu Asp Pro Ala Ala Asn Lys Ala Arg Lys
     45                  50                  55

GAA GCT GAG TTG GCT GCT GCC ACC GCT GAG CAA TAACTAG                   234
Glu Ala Glu Leu Ala Ala Ala Thr Ala Glu Gln
 60                  65
```

(2) INFORMATION FOR SEQ ID NO:21:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:21:

```
Met Arg Gly Ser His His His His His His Gly Met Ala Ser Met Thr
 1               5                  10                  15

Gly Gly Gln Gln Met Gly Arg Asp Leu Tyr Asp Asp Asp Asp Lys Asp
             20                  25                  30

Arg Trp Ile Arg Pro Arg Asp Leu Gln Leu Val Pro Trp Asn Ser Lys
         35                  40                  45

Leu Asp Pro Ala Ala Asn Lys Ala Arg Lys Glu Ala Glu Leu Ala Ala
     50                  55                  60

Ala Thr Ala Glu Gln
 65
```

(2) INFORMATION FOR SEQ ID NO:22:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
ATGCTTTTAT CCAAAAAATC AGCTACCTTT GCACTCAGTG TATTTGCGAT GCTTTTCACT       60

AGTGTAGCTC TTGCCAAAGA GGCACCACAA GCTCACAAAG CTGTGGAATT AAGTATTTTG      120

CACATCAATG ATCACCATTC TTATTTAGAA CCG                                   153
```

(2) INFORMATION FOR SEQ ID NO:23:

```
    (i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ACCATGGGGG GTTCTCATCA TCATCATCAT CATGGTATGG CTAGCATGAC TGGTGGACAG        60

CAAATCGGTC GGGATCTGTA CGACGATGAC GATAAGGATC CGAGC                       105
```